US011016057B2

(12) United States Patent
Ver Meer et al.

(10) Patent No.: US 11,016,057 B2
(45) Date of Patent: May 25, 2021

(54) PULSE-FIELD MULTIPLEX CAPILLARY ELECTROPHORESIS SYSTEM

(71) Applicant: Agilent Technologies, Inc., Santa Clara, CA (US)

(72) Inventors: Mark R. Ver Meer, Des Moines, IA (US); Jolita J. Uthe, Ames, IA (US); Wei Wei, Ames, IA (US); Martin Chris Foster, Nevada, IA (US); Bruce R. Boeke, Ames, IA (US)

(73) Assignee: Agilent Technologies, Inc., Santa Clara, CA (US)

( * ) Notice: Subject to any disclaimer, the term of this patent is extended or adjusted under 35 U.S.C. 154(b) by 94 days.

(21) Appl. No.: 15/634,846

(22) Filed: Jun. 27, 2017

(65) Prior Publication Data
US 2018/0038827 A1 Feb. 8, 2018

Related U.S. Application Data

(63) Continuation-in-part of application No. 14/984,039, filed on Dec. 30, 2015, now abandoned, which is a
(Continued)

(51) Int. Cl.
*G01N 27/447* (2006.01)
*C12N 15/10* (2006.01)
*C12Q 1/6806* (2018.01)

(52) U.S. Cl.
CPC ... *G01N 27/44713* (2013.01); *C12N 15/1093* (2013.01); *C12Q 1/6806* (2013.01);
(Continued)

(58) Field of Classification Search
CPC ....... G01N 27/44704; G01N 27/44782; G01N 27/44713; G01N 27/4443;
(Continued)

(56) References Cited

U.S. PATENT DOCUMENTS 5,122,248 A   6/1992  Karger et al.
5,324,401 A   6/1994  Yeung et al.
(Continued)

FOREIGN PATENT DOCUMENTS

EP   0527652 A2   2/1993
EP   1408328 A2   4/2004
(Continued)

OTHER PUBLICATIONS

D. N. Heiger et al., Wave Form Fidelity in Pulsed-Field Capillary Electrophoresis, Anal. Chem., vol. 64, pp. 192-199 (1992).*
(Continued)

*Primary Examiner* — Maris R Kessel

(57) ABSTRACT

The invention is a multiplex, pulsed-field capillary electrophoresis instrument with the ability to analyze DNA fragments with sizes greater than 150,000 base pairs. The parallel capillary electrophoresis system allows for the simultaneous analysis of at least 12 samples while applying a pulse or varying electric field for separation. Sequences of pulse-field electric fields are iterated to achieve accurate separation of DNA smears.

20 Claims, 25 Drawing Sheets

Related U.S. Application Data continuation-in-part of application No. 14/983,985, filed on Dec. 30, 2015, now abandoned, which is a continuation-in-part of application No. 14/822,956, filed on Aug. 11, 2015, now abandoned, which is a continuation of application No. 13/470,870, filed on May 14, 2012, now Pat. No. 9,140,666, which is a continuation-in-part of application No. 29/421,549, filed on Mar. 15, 2012, now Pat. No. Des. 689,621.

(60) Provisional application No. 61/643,411, filed on May 7, 2012.

(52) U.S. Cl.
CPC .  *G01N 27/44704* (2013.01); *G01N 27/44721* (2013.01); *G01N 27/44743* (2013.01); *G01N 27/44782* (2013.01); *G01N 27/44791* (2013.01)

(58) Field of Classification Search
CPC ............ G01N 27/44791; G01N 27/447; B01L 2400/0415; B01L 2400/0421; B01D 57/02; C07K 1/28
See application file for complete search history.

(56) References Cited

U.S. PATENT DOCUMENTS

| | | | |
|---|---|---|---|
| 5,336,383 A * | 8/1994 | Allington | G01N 27/44773 204/458 |
| 5,582,705 A | 12/1996 | Yeung et al. | |
| 5,695,626 A | 12/1997 | Yeung et al. | |
| 5,861,806 A | 1/1999 | Vories et al. | |
| 5,900,934 A | 5/1999 | Gilby et al. | |
| 6,013,166 A | 1/2000 | Heller | |
| 6,027,627 A | 2/2000 | Li et al. | |
| 6,329,139 B1 | 12/2001 | Nova et al. | |
| 6,828,567 B2 | 12/2004 | Amirkhanian et al. | |
| 6,833,062 B2 | 12/2004 | Kennedy et al. | |
| 7,118,659 B2 | 10/2006 | Kurt et al. | |
| 7,534,335 B2 | 5/2009 | Kennedy et al. | |
| 7,834,278 B1 | 11/2010 | Zeiss et al. | |
| 8,216,512 B2 | 7/2012 | Winther et al. | |
| 2001/0023825 A1 | 9/2001 | Frumin et al. | |
| 2001/0040094 A1 | 11/2001 | Inaba et al. | |
| 2002/0108857 A1 | 8/2002 | Paschetto et al. | |
| 2003/0062265 A1 | 4/2003 | King et al. | |
| 2004/0168919 A1 | 9/2004 | Kurt et al. | |
| 2005/0067285 A1 | 3/2005 | Inaba et al. | |
| 2006/0006066 A1 | 1/2006 | Yamazaki et al. | |
| 2006/0006068 A1 | 1/2006 | Desmond et al. | |
| 2008/0217177 A1 | 9/2008 | Inaba et al. | |
| 2009/0211911 A1 | 8/2009 | Ohura et al. | |
| 2010/0126857 A1 | 5/2010 | Polwart et al. | |
| 2010/0314447 A1 | 12/2010 | Zimmermann | |
| 2013/0292250 A1 | 11/2013 | Boeke et al. | |
| 2014/0116159 A1 | 5/2014 | Zimmerman et al. | |
| 2015/0346151 A1 | 12/2015 | Boeke et al. | |
| 2016/0109406 A1 * | 4/2016 | Boeke | G01N 27/44782 506/39 |
| 2016/0109474 A1 | 4/2016 | Boeke et al. | |

FOREIGN PATENT DOCUMENTS

| | | |
|---|---|---|
| EP | 1530716 B1 | 5/2005 |
| JP | 69714 A | 1/1994 |
| JP | H06300690 A | 10/1994 |
| JP | 2006515428 A | 5/2006 |
| JP | 3136062 U | 10/2007 |
| JP | 2008122169 A | 5/2008 |
| WO | 031317 A1 | 5/2001 |
| WO | 03062810 A1 | 7/2003 |
| WO | 03072250 A3 | 9/2003 |
| WO | 2004059441 A2 | 7/2004 |

OTHER PUBLICATIONS

Magnusdottir et al., "Electrohydrodynamically Induced Aggregation During Constant and Pulsed Field Capillary Electrophoresis of DNA," Biopoloymers, vol. 49, 385-401, John Wiley & Sons, Inc., 1999.

Unknown: "Membrane Potentiometers Simplify Position Sensing", Design World, May 12, 2010 (May 12, 2010), pp. 1-2, XP055418956, Retrieved from the Internet: URL:http://www.designworldonline.com/membrane-potentiometers-simplify-position-sensing/#_ [retrieved on Oct. 25, 2017].

Advanced Analytical Technologies, Inc., PCT/US2018/039668 filed Jun. 27, 2018, "The International Search Report and the Written Opinion of the International Searching Authority, or the Declaration", 13 pages, dated Oct. 23, 2018.

Sensabaugh, G.F., "Massively Parallel DNA Typing by Capillary Array Electrophoresis", Forensic Science Group, University of California Berkeley, www.ncjrs.gov/pdffiles1/Digitization/173057NCJRS.pdf, 85 pages, 1997.

Advanced Analytical Technologies, Inc., in connection with PCT/US2017/015978 filed Feb. 1, 2017, "The International Search Report and the Written Opinion of the International Searching Authority, or the Declaration", 7 pages, dated Apr. 24, 2017.

Advanced Analytical Technologies, Inc., in connection with application 18275121.4 filed Aug. 14, 2018, "The Extended European Search Report", 9 pages, dated Feb. 6, 2019.

Advanced Analytical Technologies, Inc., in connection with application 18275121.4 filed Aug. 14, 2018, "The Partial European Search Report", 11 pages, dated Nov. 2, 2018.

"Applied Biosystems—by Life Technologies", http://www6.appliedbiosystems.com/products/abi3730xlspecs.cfm, 4 pages, accessed Feb. 24, 2014.

Advanced Analytical Technologies, Inc., in connection with application 17733954.6 filed Feb. 1, 2017, "The Extended European Search Report", 5 pages, dated Jul. 31, 2019.

* cited by examiner

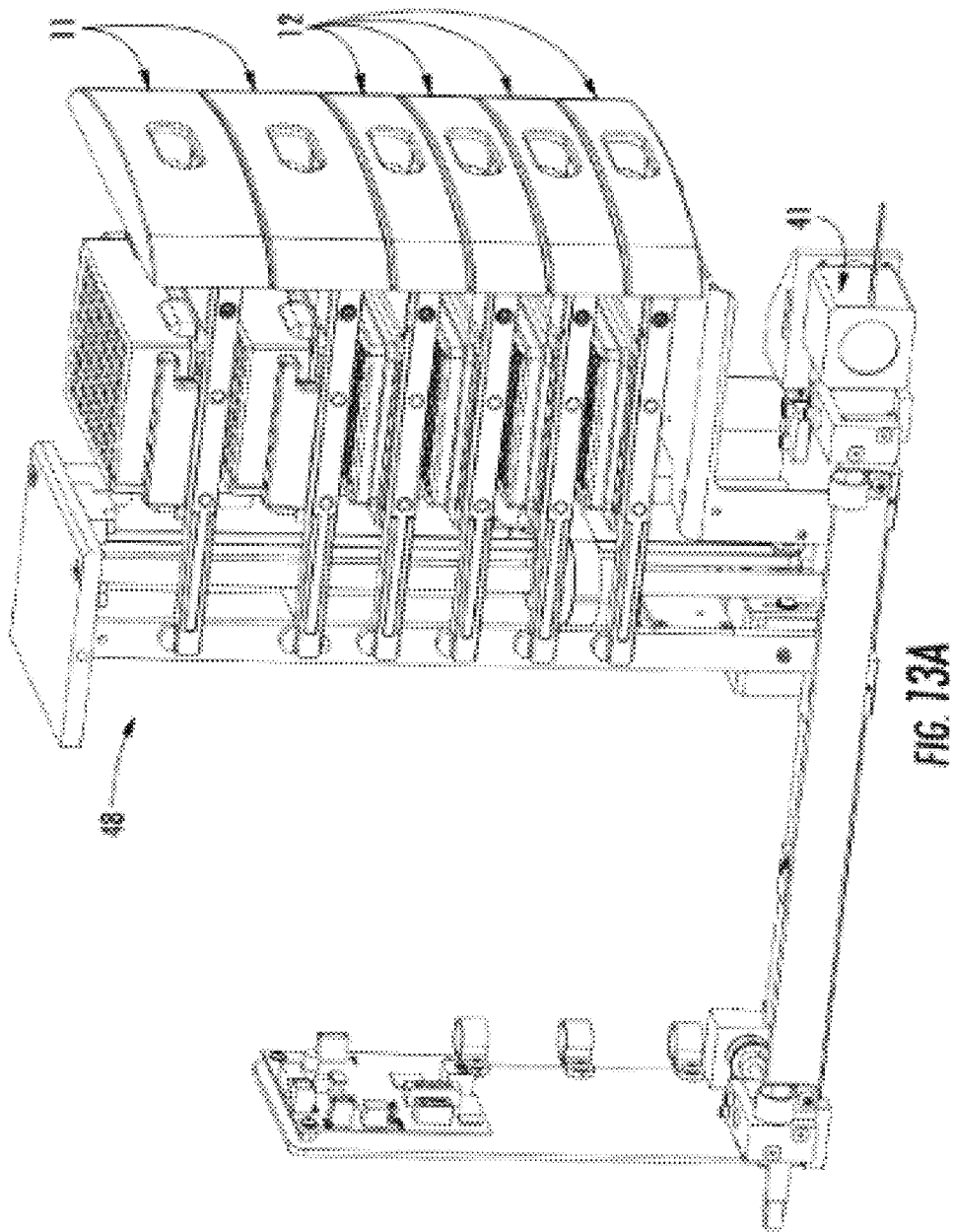

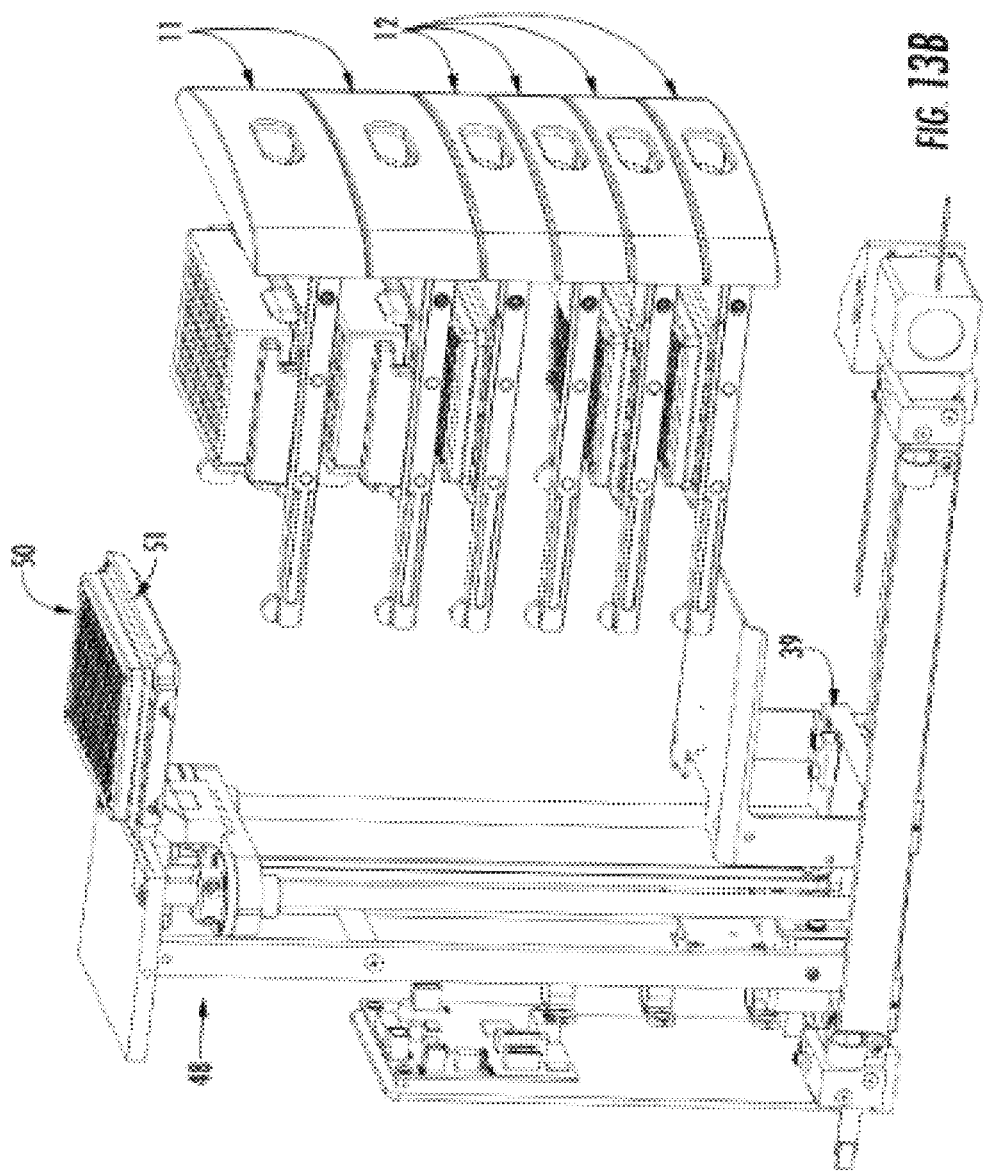

PULSE-FIELD MULTIPLEX CAPILLARY ELECTROPHORESIS SYSTEM

CROSS REFERENCE TO RELATED APPLICATION

This application is a continuation-in-part of U.S. Ser. No. 14/984,039 filed Dec. 30, 2015, which is a continuation-in-part of U.S. Ser. No. 14/983,985, filed Dec. 30, 2015, is a continuation-in-part of U.S. Ser. No. 14/822,956, filed Aug. 11, 2015, which is a continuation of U.S. Ser. No. 13/470,870, filed May 14, 2012, now U.S. Pat. No. 9,140,666, issued Sep. 22, 2015, which claims priority to provisional application Ser. No. 61/643,411, filed May 7, 2012, which is a continuation-in-part of U.S. design application Ser. No. 29/421,549, filed Mar. 15, 2012, now U.S. Pat. No. D689,621, issued on Sep. 10, 2013; all of which are herein incorporated by reference in their entirety.

BACKGROUND OF THE INVENTION

1. Field of the Invention

This invention relates to a system and software for multi-channel pulsed-field capillary electrophoresis.

2. Description of Related Art

The current next-generation sequencing (NGS) platforms use a variety of technologies for sequencing, including pyrosequencing, ion-sequencing, sequencing by synthesis, or sequencing by ligation. Although these technologies have some minor variations, they all have a generally common DNA library preparation procedure, which includes genomic DNA quality & quality assessment, DNA fragmentation and sizing (involving mechanical shearing, sonication, nebulization, or enzyme digestion), DNA repair and end polishing, and a last step of platform-specific adaptor ligation. With a rapidly growing demand for DNA sequence information, there is a critical need to reduce the time required for the preparation of DNA libraries. Many commercial NGS systems are based on the sequencing of relatively short fragments of poly(nucleic acids), ranging from 30 base-pairs (bp) to 2000 bp in length. NGS systems based on pore or nanopore platforms use larger fragment sizes, ranging from 5000 bp or higher. In some cases, the desired fragment sizes are greater than 20,000 to 50,000 bp. Newer applications of long-range sequencers target fragment sizes of 50,000 bp to greater than 150,000 bp or longer.

A labor-intensive step in DNA library preparation is the qualification (size determination) and quantification of both un-sheared genomic DNA and downstream fragmented DNA. Existing methods for DNA fragment analysis include agarose gel electrophoresis, capillary electrophoresis, and chip-based electrophoresis. Agarose gel electrophoresis is labor intensive, requiring gel preparation, sample transfer via pipetting, and image analysis. The images obtained by agarose electrophoresis are often distorted, resulting in questionable or unreliable data. It is impossible to use agarose gel electrophoresis for accurate quantification of DNA, which means that a separate, second method (UV or fluorescence spectroscopy) is required for quantification. Finally, agarose gel electrophoresis is difficult to automate. Chip or microchip based electrophoresis provides an improvement in data quality over agarose gel electrophoresis but is still labor intensive. For example, chip-based methods require manual steps to load gel, markers and samples. Even though these microchip or chip based electrophoresis units can run a single sample in seconds or minutes, the sample and gel loading are barriers to ease-of-use, especially when running hundreds or thousands of samples. Also, existing chip-based systems are unable to quantify genomic DNA. Capillary electrophoresis (CE) offers advantages over both agarose electrophoresis and microchip electrophoresis in that gel-fill and sample loading is automated.

Standard constant electric field microchip and capillary electrophoresis systems will typically report DNA size values of no greater than 50,000 bp, even though the DNA fragments may be much larger. Thus, standard microchip and capillary electrophoresis systems are limited in their ability to accurately measure DNA fragment sizes above about 50,000 bp. Newer sequencing technology requires analysis of input DNA with sizes greater than about 50,000 bp.

The standard method for the analysis of large fragments or smears of DNA is Slab-Gel Pulsed-Field Gel Electrophoresis (PFGE) where DNA with size ranges from less than 1000 base pair (bp) to several million bp can be separated and accurately sized. A major limitation in PFGE is sample throughput, because the time required for analysis can range from several hours to several days, depending on the size range of interest and the complexity of sample preparation.

The technology of alternating, pulsed fields has been extended from PFGE to single-capillary electrophoresis, with the goal of decreasing analysis time of large DNA fragment from the hours/days of PFGE to less than two hours. For example, Karger in U.S. Pat. No. 5,122,248 describes a single-capillary pulsed field capillary electrophoresis system (PFCE). Magnusdottir et. al. in "Electrohydrodynamically Induced Aggregation During Constant and Pulsed Field Capillary Electrophoresis of DNA" (Biopolymers, Vol 49, 385-401, 1999) describe a PFCE system. Although these pulsed-field single capillary electrophoresis have been shown to measure DNA fragments up to sizes of 200,000 base pairs, the throughput is limited to one sample per run. Even though the run times of capillary pulse field electrophoresis can be from less than 20 minutes to an hour, sample loads of hundreds of samples may take several hours to days to run because of the throughput restraints of a single capillary system.

The methods that have been used for pulsed-field capillary electrophoresis have relied generally on the application of simple, single alternating waveforms, for example a square wave or a sine wave applied at fixed or varying frequencies, or with different duty cycles, with a forward voltage time differing in from the reverse voltage time. Although these single-waveform methods with fixed or varying frequencies often give acceptable results when analyzing individual DNA fragments, which give sharp electropherogram peaks, these methods will not generally give accurate results when complex DNA agglomerates or DNA smears are run. DNA agglomerates or smears are broad, ill-defined peaks that are very sensitive to the pulsing methods utilized. Sizing results obtained with simple single waveforms on a pulse-field capillary electrophoresis system may give results that are significantly different than results obtained using standard Pulse Field Slab Gel Electrophoresis (PFGE). For example, the average smear size for a DNA smear measured with a single-frequency square-wave capillary electrophoresis system is usually at least 10-20% smaller than what is measured on standard pulsed-field slab electrophoresis systems. Also, simple single waveform methods, when applied to complex DNA mixtures, often result in anomalous system peaks that don't accurately represent the sample under analysis.

There is thus a need for pulse-field capillary electrophoresis systems that can run multiple samples simultaneously, and that can analyze broad DNA-smears and generate gel images or electropherograms that are equivalent to those obtained with standard Pulsed-Field Gel Electrophoresis (PFGE)

Multiplex capillary electrophoresis is known. For example, Kennedy and Kurt in U.S. Pat. No. 6,833,062 describe a multiplex absorbance based capillary electrophoresis system and method. Yeung et al. in U.S. Pat. No. 5,324,401 describe a multiplex fluorescent based capillary electrophoresis system. Although these systems offer the advantage of analyzing multiple samples simultaneously, and can run several plates sequentially, they lack the ability to load or change multiple sample plates while the system is running, and they also lack a simple workflow for efficient sample analysis. Furthermore, these multiplex systems lack the ability to measure nucleic acid fragment sizes above about 50,000 bp.

A limitation of prior-art pulsed-field capillary electrophoresis systems is the lack of an option for environmental temperature control. Temperature can affect run-to-run performance and the long-term reliability of capillary pulse-field systems. Thus, there is a need for a multiplex pulsed-field capillary electrophoresis systems that have an option for carefully controlled environmental temperature control.

While existing commercial CE systems can be automated with a robotic system, stand-alone systems are not fully automated or lack the sensitivity and data quality required for adequate DNA library analysis. An example of a CE instrument with a robot-capable interface is given by Kurt et al. in U.S. Pat. No. 7,118,659. For the construction of DNA libraries, as well as other applications such as mutation detection, it is often necessary to run thousands of samples per day, but the implementation of a robotic system for sample handling is prohibitively expensive, and many labs lack the expertise necessary for the maintenance and operation of sophisticated robotic systems. Automated forms of micro-slab-gel electrophoresis have been developed, such as those described in United States Patent Application number 20100126857. These allow for automatic analysis of multiple samples, but the techniques either still require significant human intervention, or they do not have the throughput required for high-volume applications. Amirkhanian et al. in U.S. Pat. No. 6,828,567 describe a 12-channel multiplex capillary electrophoresis system capable of measuring up 12 samples at a time using multiplex capillary electrophoresis. However, this system is not capable of measuring multiple 96-well plates, and does not have the workflow that allows the analysis of thousands of samples per day.

As can be seen, there a need for an automated capillary electrophoresis system that a) eliminates the complexity, cost, and required expertise of a robotic system b) enables users to run from one to several thousand samples per day c) allows users to conveniently load several plates or samples onto a capillary electrophoresis system while the system is running other samples d) has the small size and footprint of a stand-alone capillary electrophoresis unit and e) allows users to accurately determine the size of DNA fragments larger than 50,000 bp, and preferably larger than 100,000 bp.

This invention has, as a primary objective, the fulfillment of the above described needs.

BRIEF SUMMARY OF THE INVENTION

The present invention is a pulse-field capillary electrophoresis system with the ability to apply a varying or pulsed electric field to at least 2 and preferably at least 12 capillaries simultaneously.

The present invention also includes application of complex waveforms, which is defined as the application of sequences of simple waveforms that are iterated for the duration of the analytical run.

A preferred method for obtaining high-quality separations of complex DNA smears using multiplex pulsed-field parallel capillary electrophoresis is to apply different variable voltage waveform patterns, in sequence, over time, in repeated iterations. For example, a preferred separation method is to apply a square wave for a period of time followed by a triangle wave for a period of time, and then repeating the square-wave and triangle wave sequence for several iterations. This is shown in FIG. 18A, with a square wave applied for a period of time, T1, followed by a triangle wave, applied for a period of time, T2. In the case shown in FIG. 18A, the frequency of the applied square wave varies from slow to fast, while the frequency of the triangle wave is constant. FIG. 18B shows a sine wave (fixed frequency) applied for a period of time, T1, a followed by a square wave of varying frequency for a period of time T2. The T1+T2 sequence is iterated for "I" times to obtain a total run time of I(T1+T2) minutes. Another example is to apply a square wave for a period of time followed by a constant voltage for a period of time, and then iterating the square-wave and constant voltage sequence for several iterations. Another preferred aspect of the invention is to apply at least three different waveforms over the period of the electrophoresis separation. For example, the application of a triangle wave, followed by a square wave, followed by a sine wave, with the sequence of the three waveforms iterated multiple times. Another preferred aspect of the invention is to iterate two different waveforms, followed by a third waveform. For example, the application of a triangle wave, followed by a square wave, the sequence of which is iterated several times, followed by the application of a square wave for a fixed period of time. Another example is to apply a square wave, for a first period of time, a constant voltage for a second period of time, and triangle wave for a third period of time, in sequential segments, and iterate the sequence multiple times until the electrophoresis run is complete.

Another aspect of the invention is a method of applying an electric field across at least two capillaries, comprising; applying a first pulse-field waveform at a first frequency across said capillaries for a first period of time; applying at least a second, different shape pulse-field waveform at a second frequency across said capillaries for a second period of time; and thereafter repeating the said first and at least second pulse-field waveforms at least twice; wherein said first frequency varies with time within said first period of time and said second frequency varies with time within said second period of time.

BRIEF SUMMARY OF THE DRAWINGS

FIG. 13A shows a view of the x-z stage relative to the drawers.

FIG. 13B shows a view of the x-z stage with a sample tray lifted.

DETAILED DESCRIPTION OF THE INVENTION

The invention is a multiplexed pulsed-field capillary electrophoresis system with enhanced workflow. The capillary electrophoresis system and apparatus of the present invention includes an absorbance or fluorescence-based capillary electrophoresis sub-system with a light source, a method for carrying light from the light source to the sample windows of a multiplex capillary array containing at least 12 capillaries (preferably 96 capillaries), and a method for detecting light emitted (fluorescence) or absorbed (absorbance) from the sample windows of a multiplex array. The sub-system also includes a method for pumping buffers and gels through the capillaries, as well as a method for application of an electric field for electrophoretic separation. The optics of the fluorescent-based sub system of the present invention are described by Pang in United States Patent Applications 20070131870 and 20100140505, herein incorporated by reference in their entirety. The optics of an applicable absorbance-based system, as well as the fluid handling, reservoir venting, application of electric field, and selection of fluids via a syringe pump and a 6-way distribution valve are discussed by Kennedy et al. in U.S. Pat. Nos. 7,534,335 and 6,833,062, herein incorporated by reference their entirety.

Figure 1:
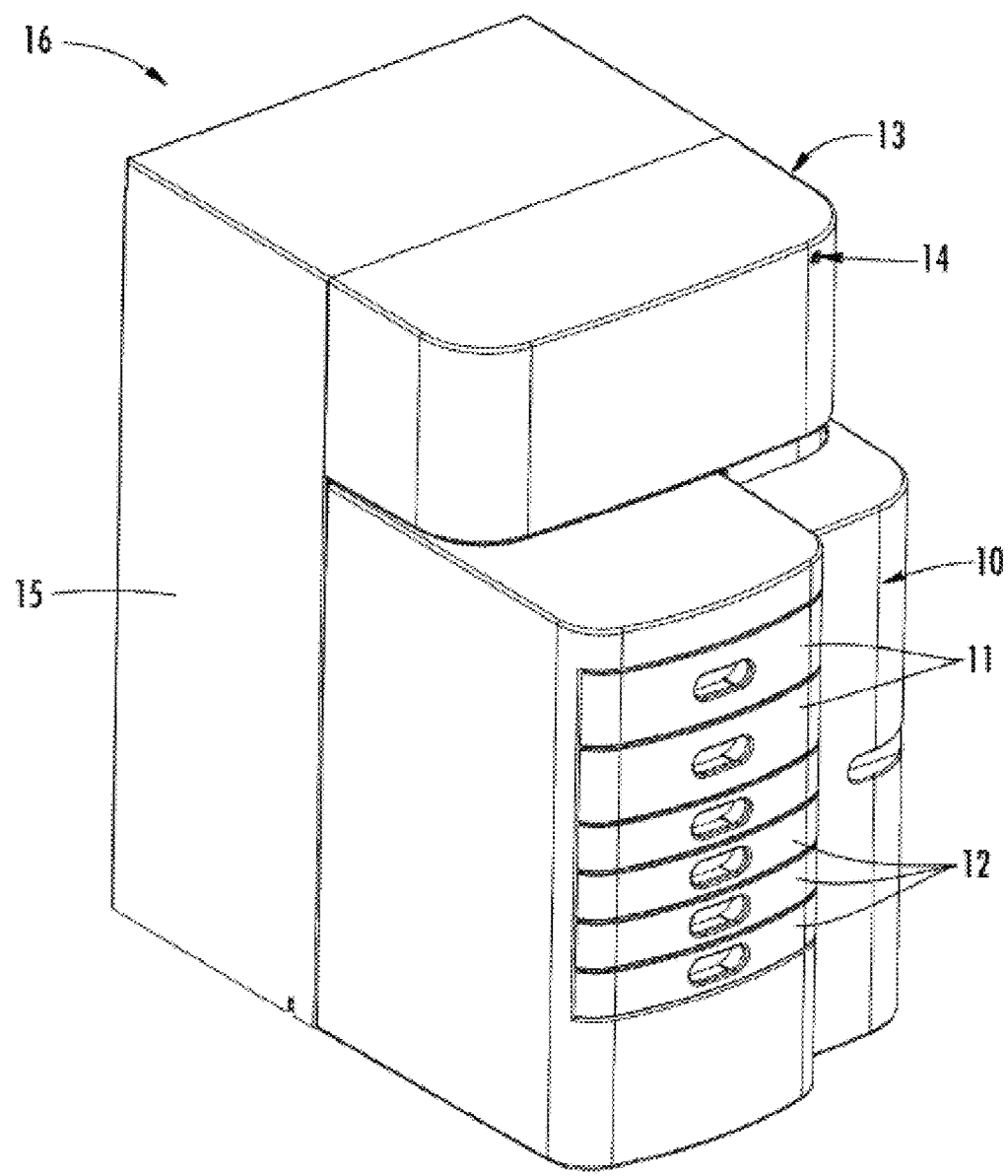
FIG. 1 shows a left-front-view of the instrument, with 6 drawers for holding sample and buffer plates.

Referring to FIG. 1 the multiplex capillary system (or unit or instrument) and/or console 16, with enhanced workflow has a door 10 for easy access to the loading of gels, two drawers 11 for the easy loading of a buffer tray and a waste tray. Drawers 12 can be opened for easy loading of 96 well PCR plates, tube strips, vials, or other sample containers. A top door 13 can be opened to access a replaceable capillary array, array window, and capillary reservoir. An indicator light 14 is used to for notifying users of the active application of a high-voltage for electrophoresis. A removable back-panel 15 allows access to electronics such as a high-voltage power supply, electrical communication panels, a pump board, pressure transducer board, and stage driver electronics. The back panel 15 also allows maintenance access to the x-z stage, which is used to move sample trays from the drawers 11 and 12 to a capillary array.

Figure 2:
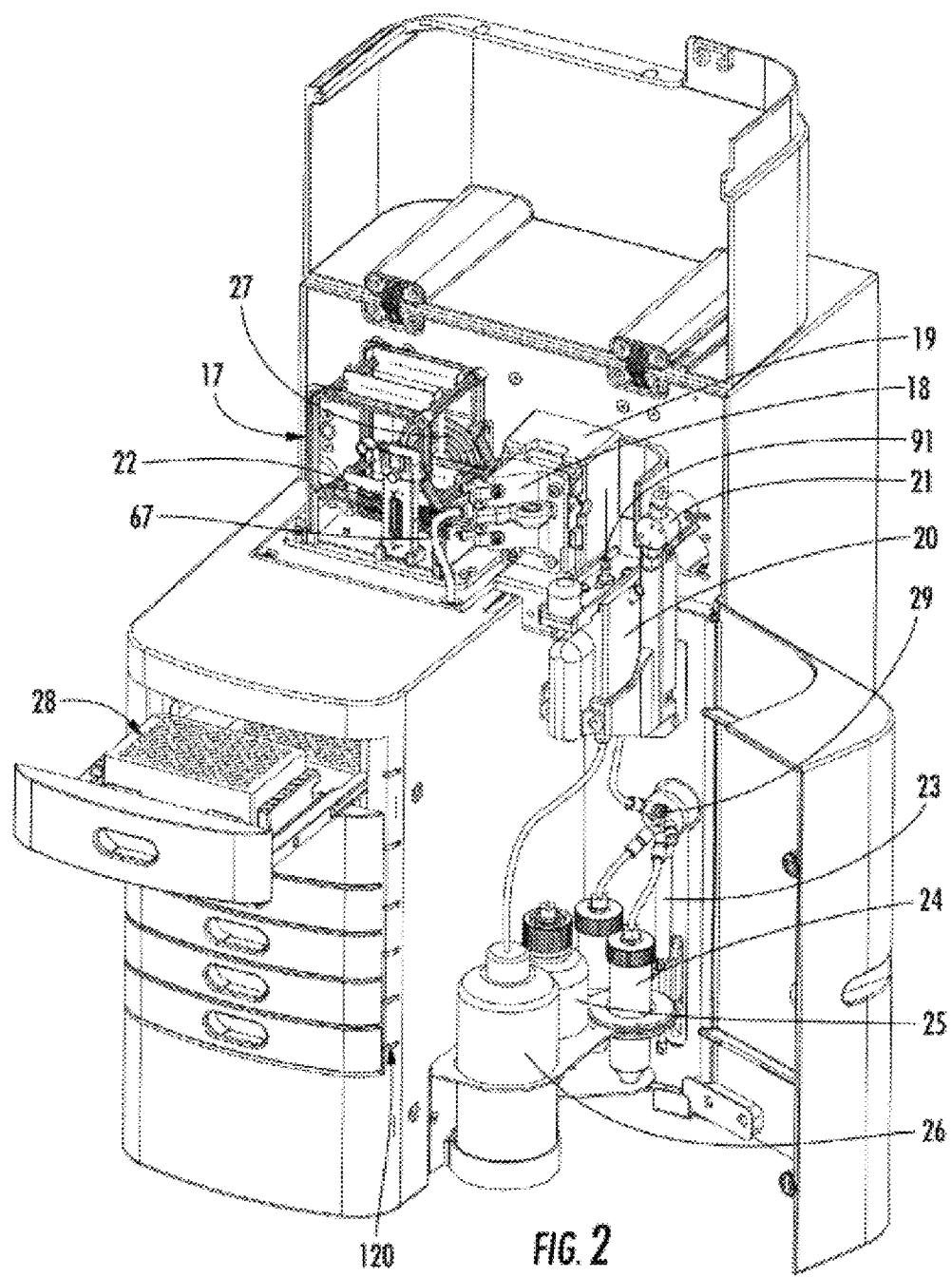
FIG. 2 shows a right-front view of the instrument with one drawer pulled out for placement of a buffer plate and the top and side door compartments open.

FIG. 2 shows the multiplex capillary system used with the enhanced workflow console 16 with the top and side doors open. A replaceable capillary array (cartridge) 17 holds either 12 or 96 capillaries for multiplex capillary electrophoresis. An LED light guide 67 guides light from a LED engine located in the back compartment to the array window block 22 which is inserted between the array window holder 19 and LED light guide and window holder 18. In this view, array window block 22 is attached to the capillary array 17 for display. When the capillary array 17 is removed from the system 16, the array window block 22 can be attached to the capillary array 17 (as shown). When the capillary array 17 is fully installed, the array window block 22 is not visible because it is sandwiched between the array window holder 19 and LED light guide and window holder 18. A vent valve 21 is connected to the top of a capillary reservoir 20. A syringe pump 23 coupled with a 6-way distribution valve 29 delivers fluids and electrophoresis gels from fluid containers 24 and 25 into the capillary reservoir 20, waste container 26, or capillaries in the capillary array 17. A fan 27 is used for forcing cool air from the back compartment through the capillary array 17, past the outside of the capillary reservoir 20, down past the fluid containers 24, 25 and finally out the bottom of the instrument. LED indicator lights 120 are used to indicate the presence or absence of trays in the drawers. A buffer tray 28 is shown in a drawer (11, FIG. 1). The capillary array reservoir tip 91 is shown inserted into the capillary reservoir 20.

The concepts and practical implementation of motion control systems are known. For example, Sabonovic and Ohnishi; "Motion Control" John Wiley and Sons, 2011, herein incorporated by reference in its entirety, discusses practical methods for the design and implementation of motion control. It does not, however, show an enhanced CE workflow console 16 as depicted here.

Figure 3:
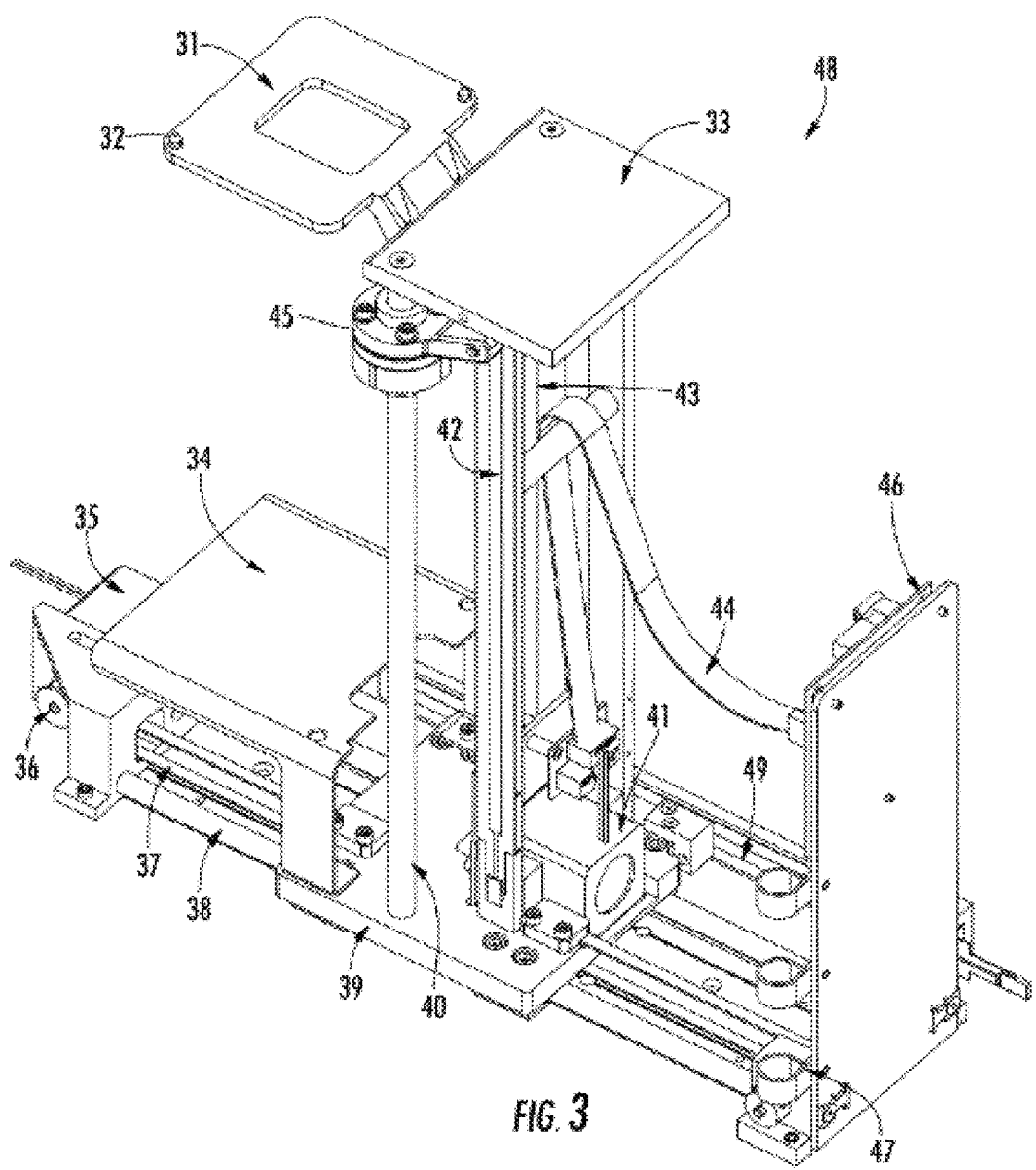
FIG. 3 shows the x-z stage assembly.
Figure 8:
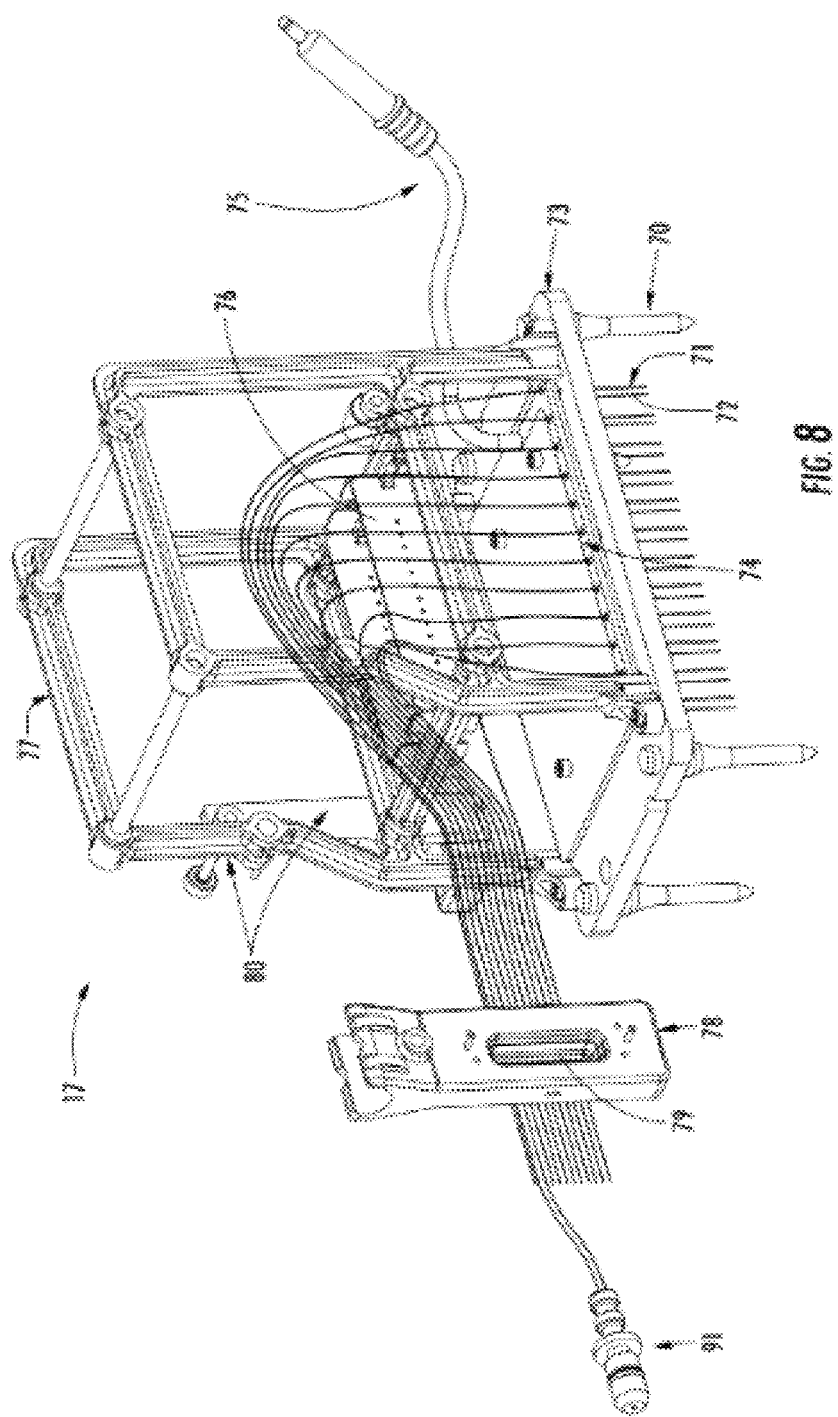
FIG. 8 shows a capillary array cartridge

FIG. 3 shows the x-z stage assembly 48, which is used to transport sample plates or trays (50, FIG. 4) and associated tray holders (51, FIG. 4) from the drawers (12 FIG. 1) to the injection capillaries (72, FIG. 8) and injection electrodes (71, FIG. 8) of the capillary array (17, FIG. 8). The x-z stage assembly 48 is also used to position a buffer tray or waste tray (28, FIG. 2) from the drawers (11, FIG. 1) to the injection capillaries 72 and injection electrodes 71 of the capillary array 17 (FIG. 8). The x-z stage assembly 48 has a tray carrier 31 with alignment pins 32, which align with holes (57, FIG. 5) on the bottom of the tray holder (51, FIG. 4) to prevent subsequent sliding or movement of the tray holders 51 during transport. A protective cover 34, made of metal or plastic, is used to prevent gels or other liquids from spilling onto the x-direction guide rails 38 and x-direction drive belt 37 of the x-z stage assembly 48. An x-drive stepper motor 35 is used as the electro-mechanical driver for motion in the x-direction. A drive pulley 36 is attached to the stepper motor 35 and x-direction drive belt 37 which drives the stage carrier 39 back-and forth along the guide-bars 38. A second drive pulley (not shown) is used on belt 37 towards the back-end of the stage, which allows the belt 37 to make a full loop when affixed to stage carrier 39. Any motor-induced movement of the belt 37 induces an x-direction movement of the stage carrier 39 on the guide rails 38. A stepper-motor for the z-position is located at 41, which is attached to a drive pulley/belt configuration similar to that shown in the x-direction. The z-direction drive belt is shown as 43. The z-position motor/pulley/belt is used to move the tray carrier 31 up and down the guide bars 40. Top plate 33 serves as a structural support for the guide bars 40. An electrical communication strip 44 is used to communicate between an electrical motor control board 46 and the stepper motors 41 and 35. An x-direction membrane potentiometer strip 49, along with appropriate control electronics, is used to determine and control the absolute position of the stage carrier 39 in the x-direction. A z-direction membrane potentiometer strip 42, along with appropriate control electronics, is used to determine the absolute position of the tray carrier 31 in the z-direction. Linear encoders or rotational encoders (on the stepper motor 35, 41) are alternative forms of positional measurement and control. Bearings 45 are located on each guide bar 40 and guide rail 38 to enable friction-free movement of both the tray carrier 31 and the stage carrier 39. Note that there are two guide bars 40 or guide rails 38 per axis. Electrical cord guide straps 47 are attached to a back support, which also holds the electrical control board 46 for the x-z stage assembly 48.

Figure 4:
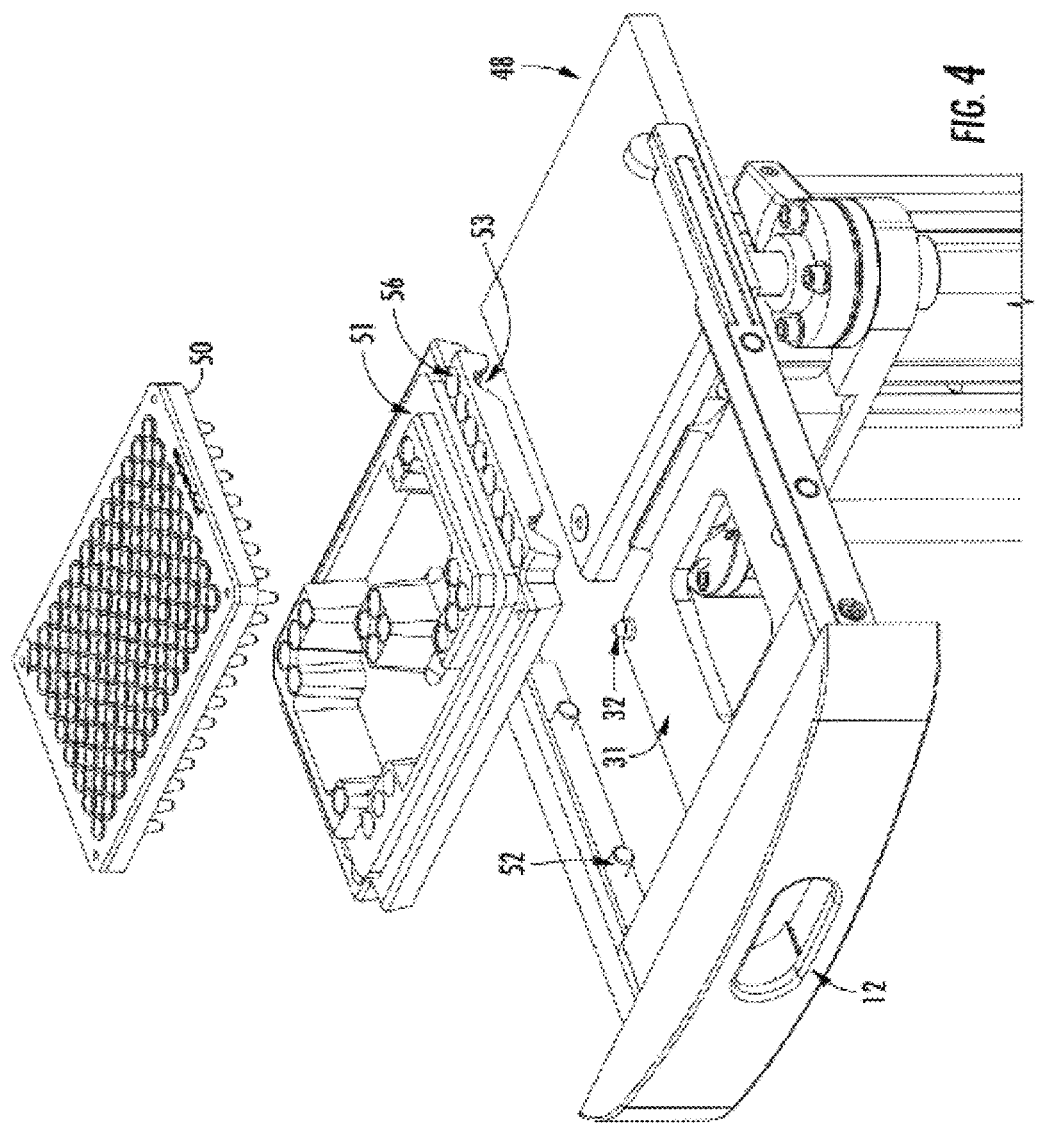
FIG. 4 shows a drawer, stage assembly, tray holder, and sample plate.
Figure 5:
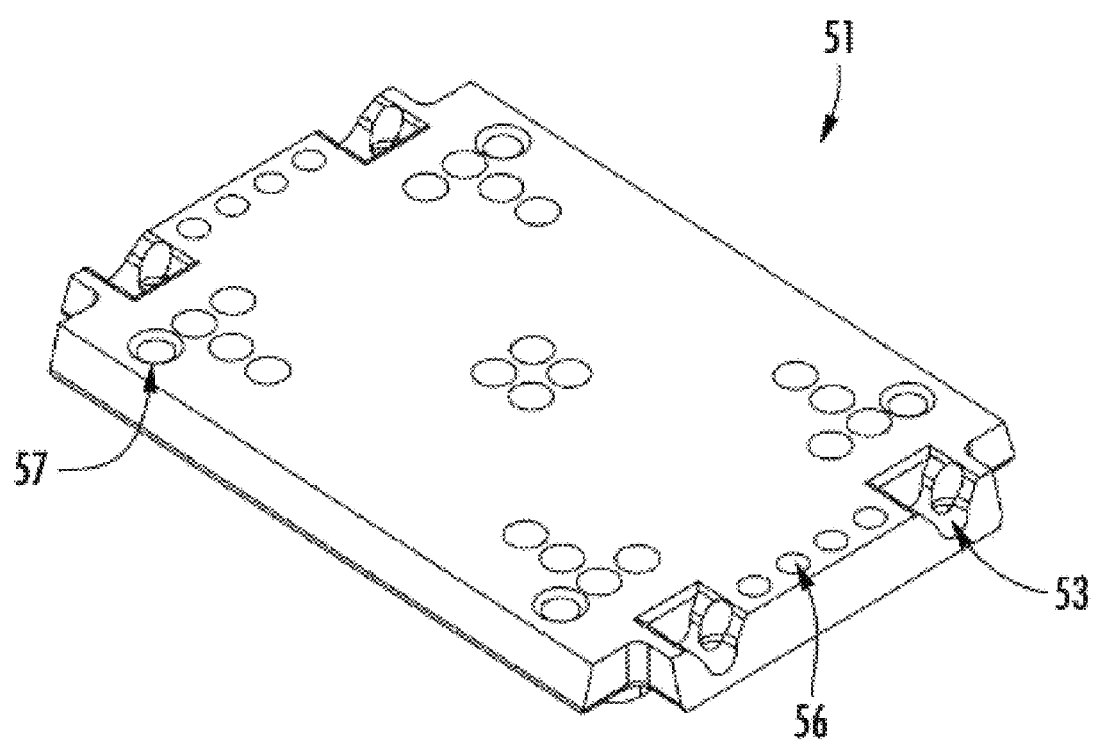
FIG. 5 shows the bottom of a tray holder.

FIG. 4 shows a drawer 12, superimposed on an image of the x-z stage assembly 48, tray holder 51, and 96-well sample tray 50. The tray holder 51 is molded to specifically hold a 96-well plate, shown here as 50. Alternative moldings of the tray holder 51 allow for different sample plates, including 384-well plates. Holes (57, FIG. 5) on the bottom of the tray holder 51 align with the alignment pins 32 of the tray carrier (31 FIG. 4). Notches 53 in the tray holder 51 align with alignment pins 52 on the drawer 12 to enable the tray holder 51 to fit in a tight, reproducible way within the sample drawer 12.

Figure 6:
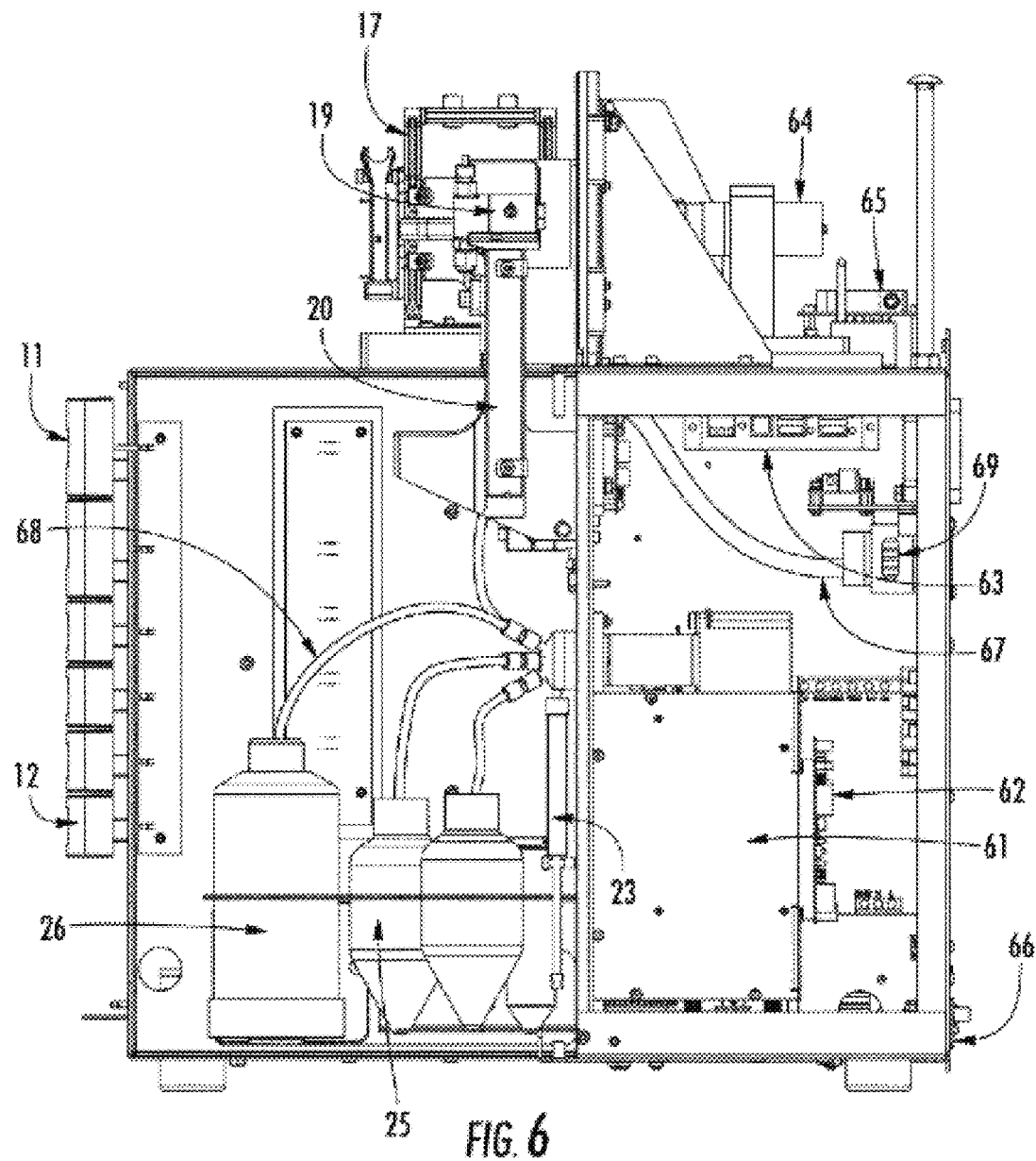
FIG. 6 shows a right-side view of the instrument without the cover.

FIG. 6 Shows a right side view of the electrophoresis system, with a chassis 66, pump motor and control system 61, pump control board 62, LED light engine 69, LED light line 67, high voltage power supply board 65, capable of applying 0.0 kV to 15 kV across the electrodes of the capillary array 17, a CCD camera 64, capillary array cartridge 17, array window holder 19, capillary reservoir 20, drawers 11, drawers 12, fluid lines 68, waste container 26, gel containers 25 and syringe 23. A USB electronic distribution bard is shown as 63.

Figure 7:
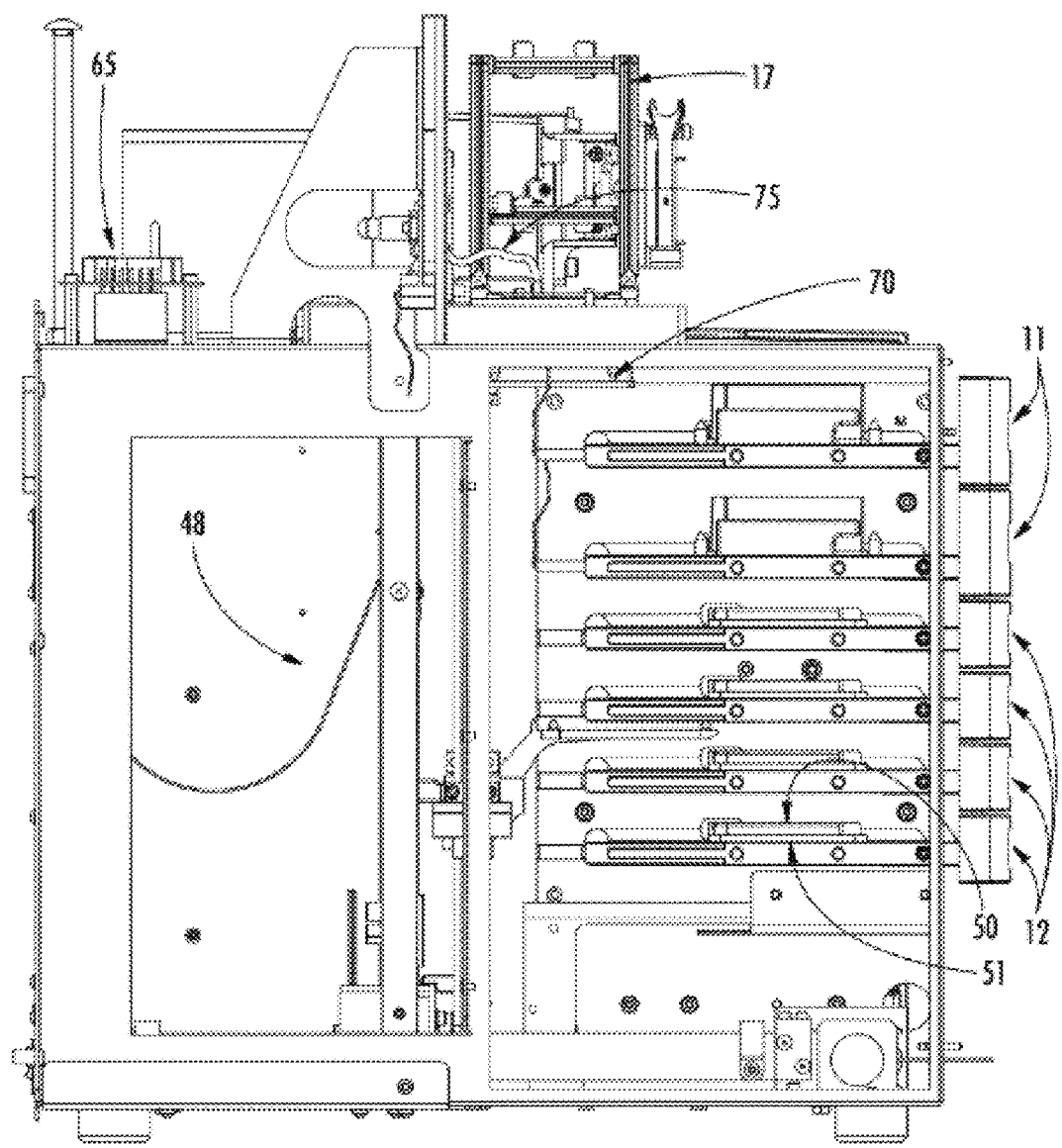
FIG. 7 shows the left-side view of the instrument without the cover.

FIG. 7 shows a left side-view of the electrophoresis unit 16 showing the x-z stage assembly 48, which moves tray holders 51 and sample trays or plates 50 from a drawer 12 or 11 to the bottom of the capillary array 17. The stage unit 48 can move the sample tray holder 51 and sample tray 50 up in the z-direction to lift the tray holder/sample tray off of the drawer 12 (or 11), move back in the x-direction away from the sample drawers 12, and then move the sample plate 50 up in the z-direction to the bottom of the capillary array 17. After electrokinetic or hydrodynamic injection, the stage unit 48 can move the sample tray holder/sample tray back down to the target drawer position (down in the z-direction), move forward in the x-direction just above the sample plate 50, and then drop down in the z-direction to set the sample tray holder/sample tray onto the drawer 12. When the sample tray holder 51 is resting in a drawer 12, the back edge of the sample tray holder 51 and sample tray 50 are aligned so that they do not lie directly underneath the capillary array 17. This allows the sample stage tray carrier (31, FIG. 3) to move up and down along the entire z-axis with a tray holder/sample tray without colliding into other tray holders/sample trays in the drawers 12. The alignment pins (70, FIG. 8) on the bottom of the capillary array 17 are used to align the tray holder 51 with a sample tray 50 so that the capillary and electrode tips (the tips of the injection capillaries 72 and the injection electrodes 71) dip into each sample well of the sample plate 50 and do not collide with other areas of the sample plate 50. This is shown in more detail in FIG. 11, which shows a sample tray holder 51 with a sample tray 50 aligned underneath a capillary array 17. Alignment holes 56 on the tray holder 51 force the alignment of the tray holder 51 with the capillary array alignment pins 70.

FIG. 7 also shows high voltage power supply board 65 and high voltage power supply cable 75 (to the capillary array 17).

FIG. 8 shows a capillary array cartridge 17, with rigid plastic support structure 77, window storage and transport screw 80, capillary support cards 76, high voltage power supply cable 75, and insulating support structure 73 onto which the electric circuit board 74 is placed. Electrodes 71 protrude through the electric circuit board 74, through the insulating support structure 73, and protrude through the bottom of the capillary array 17. The electrode material is stainless steel or tungsten. The electrode dimension, which is not a critical aspect of the invention, is 50 mm diameter by 29 mm length. The protrusion from the bottom of the cartridge base is 20.0 mm. The electrodes 71 are soldered onto the circuit board 74. The high voltage power supply cable 75 is also soldered to the same circuit of the electrical circuit board 74, which enables contact of the electrodes 71 with the high voltage power supply (65, FIG. 6). Capillary tips (the tips of the injection capillaries 72) are threaded through the electric circuit board 74 and insulated support structure 73 and are aligned immediately adjacent and parallel to the electrode tips (the tips of the injection electrodes 71). The distance between the capillary tips and electrode tips are from 0.1 mm to 4 mm. The ends of the capillary tips and the ends of the electrode tips lie in a single plane (i.e. the capillary tips and electrode tips are the substantially the same length, with length variation of no more than about +/−1 mm. Preferably, the length variation of capillary tips and electrode tips is less than 0.5 mm. The capillaries 72 thread through the bottom of the capillary array 17, through the insulating support structure 73, through the electric circuit board 74, through the capillary support cards 76 (which are supported by the rigid plastic support structure 77) through the capillary window holder 78 with capillary windows 79 centered in the opening of the window holder 78, and then finally through the capillary reservoir tip 91, in which all capillaries 72 (in this case 12) are threaded through a single hole. For 96 capillary arrays 17, capillaries 72 are threaded in groups of 12, or preferably groups of 4 in the capillary reservoir tip 79. The capillaries 72 are held in place in the reservoir tip 91 with an adhesive, such as a thermally or UV-curable epoxy.

Figure 12A:
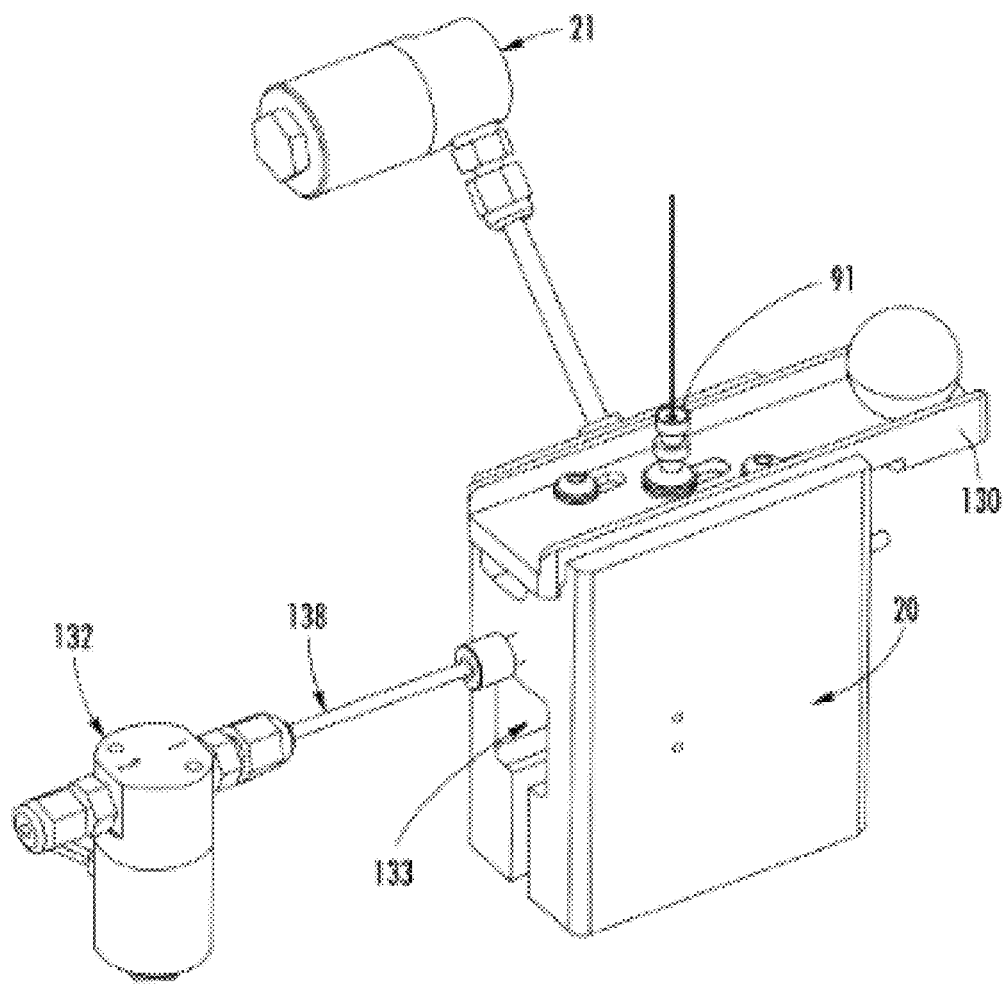
FIG. 12A shows a view of the capillary electrophoresis reservoir system.

FIG. 12A shows the capillary reservoir 20, with reservoir body (indicated by the arrow of 20), capillary reservoir tip 91, slider bar 130 (for locking capillary reservoir tip 91 into the capillary reservoir 20, through alignment of a notch on the capillary reservoir tip 91 and the slider bar 130), vent block valve 21, waste tube out 138, waste block valve 132, and pressure transducer cavity 133.

Figure 12B:
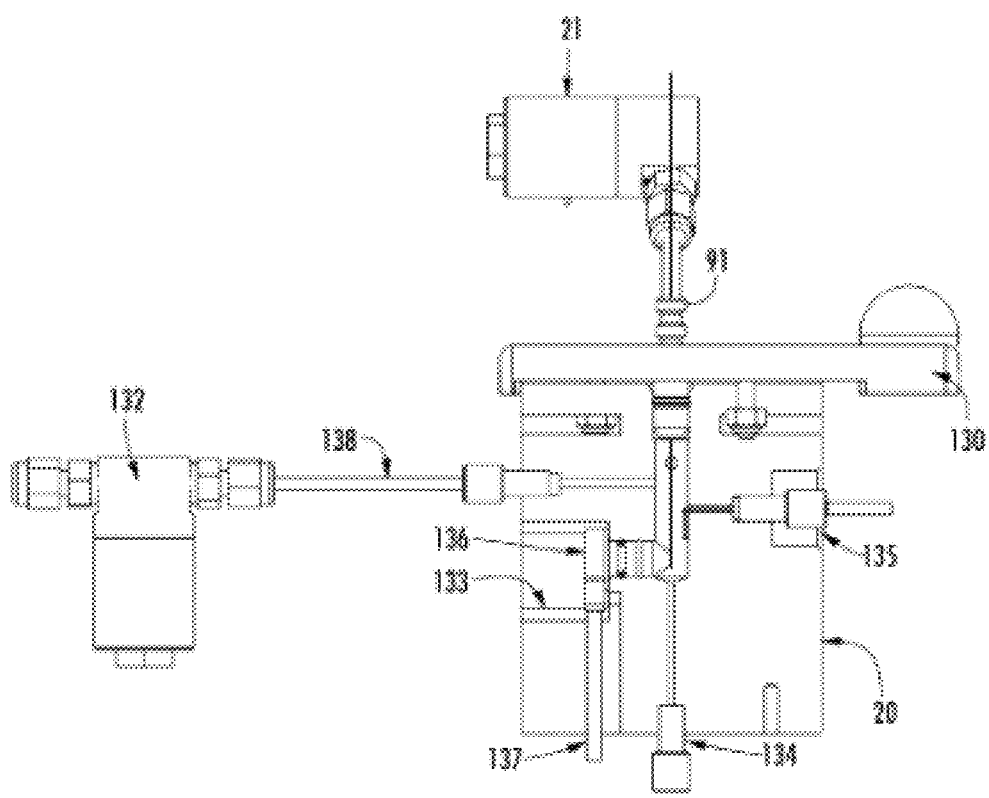
FIG. 12B shows a view of the capillary electrophoresis reservoir system.

FIG. 12B shows an alternate cut-out view of the capillary reservoir 20, with the reservoir body, capillary reservoir tip 91, slider bar 130, vent block valve 21, waste tube out 138, waste block valve 132, electrode for attachment to ground (or ground electrode) 135, pressure transducer cavity 133, pressure transducer 136, pressure transducer cable for attachment to analog/digital board 137, and fluid tube input 134 (from syringe pump 23 FIG. 2).

The reservoir body of the capillary reservoir 20 can be made of any solid material such as acrylic, Teflon, PETE, aluminum, polyethylene, ABS, or other common metals or plastics. The key criterion is that the material is durable and chemically resistant to the materials used. A preferred material is acrylic or Teflon.

Figure 11:
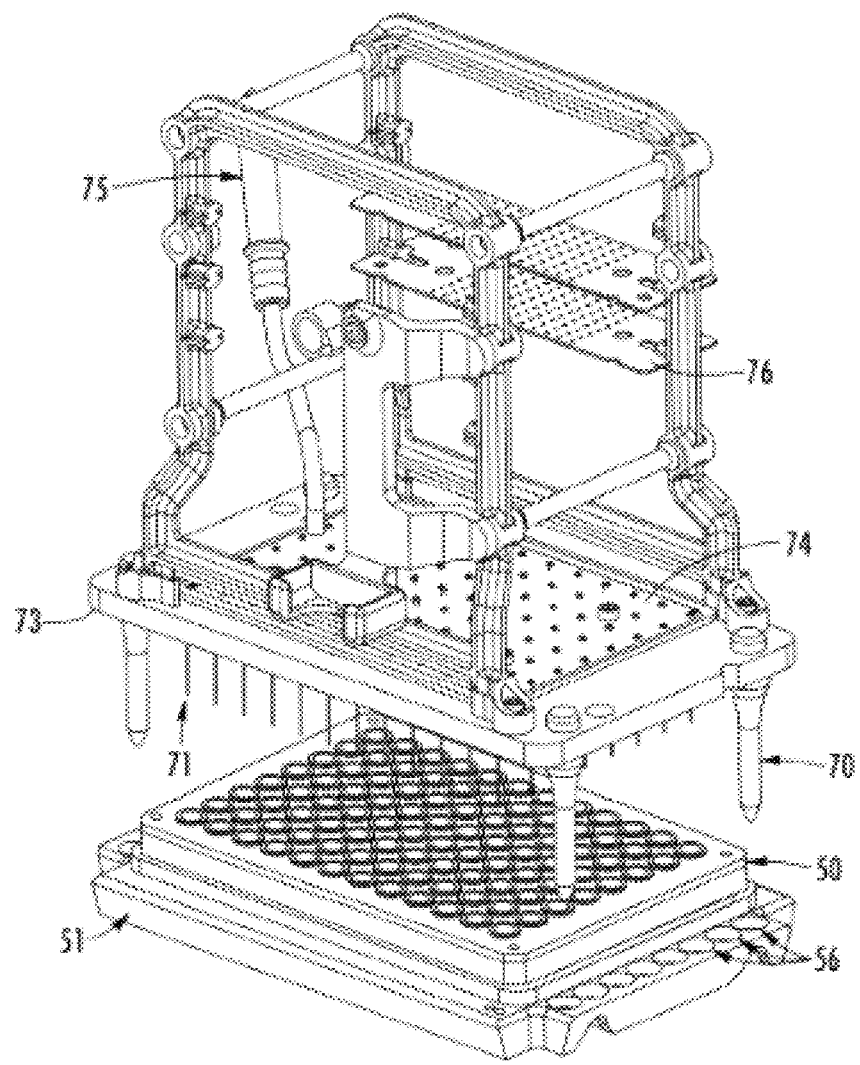
FIG. 11 shows the positioning of a sample plate under the array by the stage.

FIG. 13A shows the x-z stage unit 48 in relation to the drawers 11 and 12. The x-z stage is located directly behind the drawers 11 and 12, and can move the stage carrier (39, FIG. 13B) back-and forth in the x-direction using the stepper-motor for the x-position (35, FIG. 3). A sample tray 50 is removed from a drawer 12 (or 11) by first moving the stage forward, towards the drawers 11 and 12, in the x-direction. The tray carrier (31, FIG. 3) lifts a tray holder 51 up and off a drawer 12 in the z-direction using the z-direction stepper motor 41 (see also FIG. 3). The stage carrier 39 is then moved back in the x-direction, away from the drawers 11 and 12, as shown in FIG. 13B. The stage carrier 39 is then moved up in the z-direction to move the tray holder 51 and sample tray 50 to the injection position of the capillary array 17 (FIG. 11).

A typical strategy for pumping fluids for capillary electrophoresis is as follows. Consider the following 6 positions of the six-way distribution valve (29, FIG. 2) on the syringe pump 23. Position 1 is connected to the bottom of the capillary reservoir 20 (fluid tube input 134, FIG. 12B); position 2 is connected through a tube to a bottle of conditioning fluid (a fluid for conditioning the walls of the capillaries 72); position 3 is connected to a "Gel 1" which is used for the analysis of genomic DNA, position 4 is connected to a "Gel 2" which is used for the analysis of fragmented DNA, position 5 is unused, or optionally used to clean the vent valve via the pumping of air through the vent valve to the waste bottle and position 6 is connected to the waste bottle 26.

Step A: The capillary reservoir 20 is first emptied by opening position 1 (reservoir), filling the syringe 23 with fluid that is in the capillary reservoir 20, closing position 1, opening position 6, and emptying fluid to the waste (waste container 26). This is repeated until the capillary reservoir 20 is empty. Block valves 21 and 132 are kept open during this process to enable efficient draining of the capillary reservoir 20.

Step B: The capillary reservoir 20 is then filled with conditioning solution by opening position 2, filling the syringe 23 with conditioning solution, closing position 2, opening position 1, and filling the capillary reservoir 20 with conditioning solution. Block valve 21 is closed, but block valve 132 to waste (waste container 26) is open, enabling the over-filling of the capillary reservoir 20 with conditioning solution.

Step C: The capillaries 72 are filled by closing both vent block valve 21 and waste vent valve 132. The syringe 23 is filled with capillary conditioning solution. Position 1 is opened, and fluid is pressure filled through the capillaries 72 at a minimum of 100 psi for a pre-determined time, which may range from 1 minute to 20 minutes.

Step D: The capillary reservoir 20 is emptied by step A, and then re-filled with gel using the same process as in Step B, except that position 3 for the gel is used on the 6-way distribution valve 29.

Step E: The capillaries 72 are filled with gel using a process analogous to Step C.

After steps A-E, the capillaries 72 are ready for electrophoresis.

A general strategy and process for analyzing samples using electrophoresis is as follows.

Samples are placed into a 96-well plate (sample tray or plate 50) for analysis. The user places the sample plate 50 into a sample drawer (12, FIG. 1), and then adds jobs to a computer-based queue, corresponding to the analysis of a specific row or the entire sample plate 50 in the drawer 12. The computer, which is the control system of the instrument, executes the analysis of the row or entire sample tray 50 of interest.

A key embodiment of the invention is the workflow of the capillary electrophoresis system. Drawers (11, FIG. 1) allow easy placement of buffer and waste trays 28 into the system 16. Drawers (12, FIG. 1) allow easy placement of sample trays into the system 16. Of particular importance is the ability to place or remove sample trays 50 from drawers (12, FIG. 1) while the system 16 is performing capillary electrophoresis. Indicator lights (120, FIG. 1) show if a tray 28, 50 is present or absent in a drawer 11, 12, which let users know if a drawer 11, 12 is in place. A typical workflow for a 12-capillary multiplex system is as follows: User A walks up to the machine with sample tray 1, and places it into the third drawer from the top (one of drawers 12, FIG. 1). User "A" then fills a queue with three jobs, which correspond to performing capillary electrophoresis on the three rows of samples: sample tray 1 row A, sample tray 1 row B, and sample tray 1 row C. User "A" then instructs the computer to execute the queue, and as a result, the system begins capillary electrophoresis of sample tray 1, row A, and will continue executing jobs in the queue until there are no more jobs. User "B" then comes up and places sample tray 2 into the fourth drawer from the top (one of drawers 12, FIG. 1). User "B" then adds 8 jobs to the queue corresponding the performing of capillary electrophoresis on 8 rows of samples: sample tray 2, rows A-H. The computer will continue analyzing user "A" samples until they are finished, and then continue on with the analysis of user "B" samples. In the meantime, user "C" walks up and loads sample tray 3 into the fifth drawer from the top (one of drawers 12, FIG. 1). User "C" then adds 1 job to the queue corresponding to the analysis of 1 row of samples: sample tray 3, row A. This process can continue indefinitely, as long as there is sufficient gel in gel containers (25 in FIG. 2), or if there is sufficient run buffer in the buffer tray (28, FIG. 2) located in top drawer 11, FIG. 1. It is, among other things, the enabling of this workflow, via the drawers 11 and 12, sample stage (x-z stage assembly 48), and computer program with a queue for loading jobs that differentiates the present invention from the prior art systems for CE workflow.

An important embodiment of the present invention is a computer program that enables users to load a sample plate 50 into the desired vertical drawer (12, FIG. 1), and instruct the system 16 to run the desired rows or entire sample plate 50, while the system 16 is running other samples. This allows multiple users to load samples and/or sample plates 50, or a single user to load multiple samples and/or sample plates 50 without first having to wait for the electrophoresis of other samples to be complete.

Figure 9:
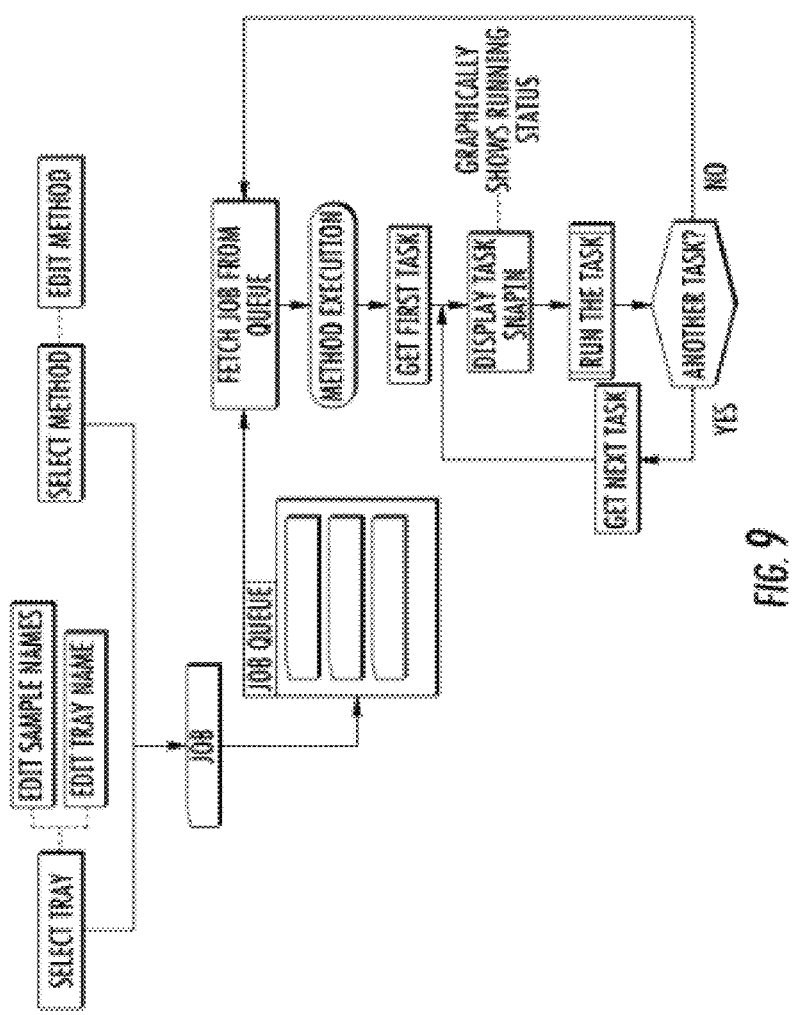
FIG. 9 shows the flow-chart for the software control program for creating a queue of jobs.

FIG. 9 shows the general flow diagram of the work process and computer program. A user loads a sample tray 50 into a drawer (12, FIG. 1) of the system 16. On the computer, the user then selects the sample tray 50, and edits the sample names and/or tray name. The user further selects or defines a method (time of separation, electric field used for separation, gel selection, etc.). This selected sample tray 50, along with an associated method is defined as a "job", which is then placed into a queue. The computer as an instrument control device, fetches jobs from the queue, and controls the instrument (system 16) for every task, including operation of the syringe pump 23, operation of the high voltage power supply 65, and the motion control stage (48, FIG. 3). For each run (or job), there may be a variety of tasks, with each task requiring direct command and control of subunits of the system 16. Tasks associated with control of the syringe pump 23 include emptying/filling the capillary reservoir 20 with conditioning fluid, and forcing conditioning fluid through the capillaries 72, emptying/filling the capillary reservoir 20 with gel, and forcing gel through the capillaries 72. Tasks associated with control of the x-z stage assembly 48 may include moving or removing a waste tray to/from the inlet side of the capillaries 72 and electrodes 71 of the capillary array 17, moving or removing a buffer tray 28 to/from the inlet capillaries and electrodes of the capillary array, or moving/removing a sample tray to/from the inlet side of the capillaries 72 and electrodes 71 of the capillary array 17. Tasks associated with control of the high voltage power supply 65 include turning off/on a high voltage for capillary electrophoresis separation. Other tasks are associated with the camera 64 (acquisition of data), and block valves 21 and 132. For each set of samples, the program will complete all tasks required to obtain a set of electropherograms. Once these tasks are complete, the program fetches another job from the queue. If the queue is empty, all sample runs are complete (until the user initiates another queue).

Figure 10:
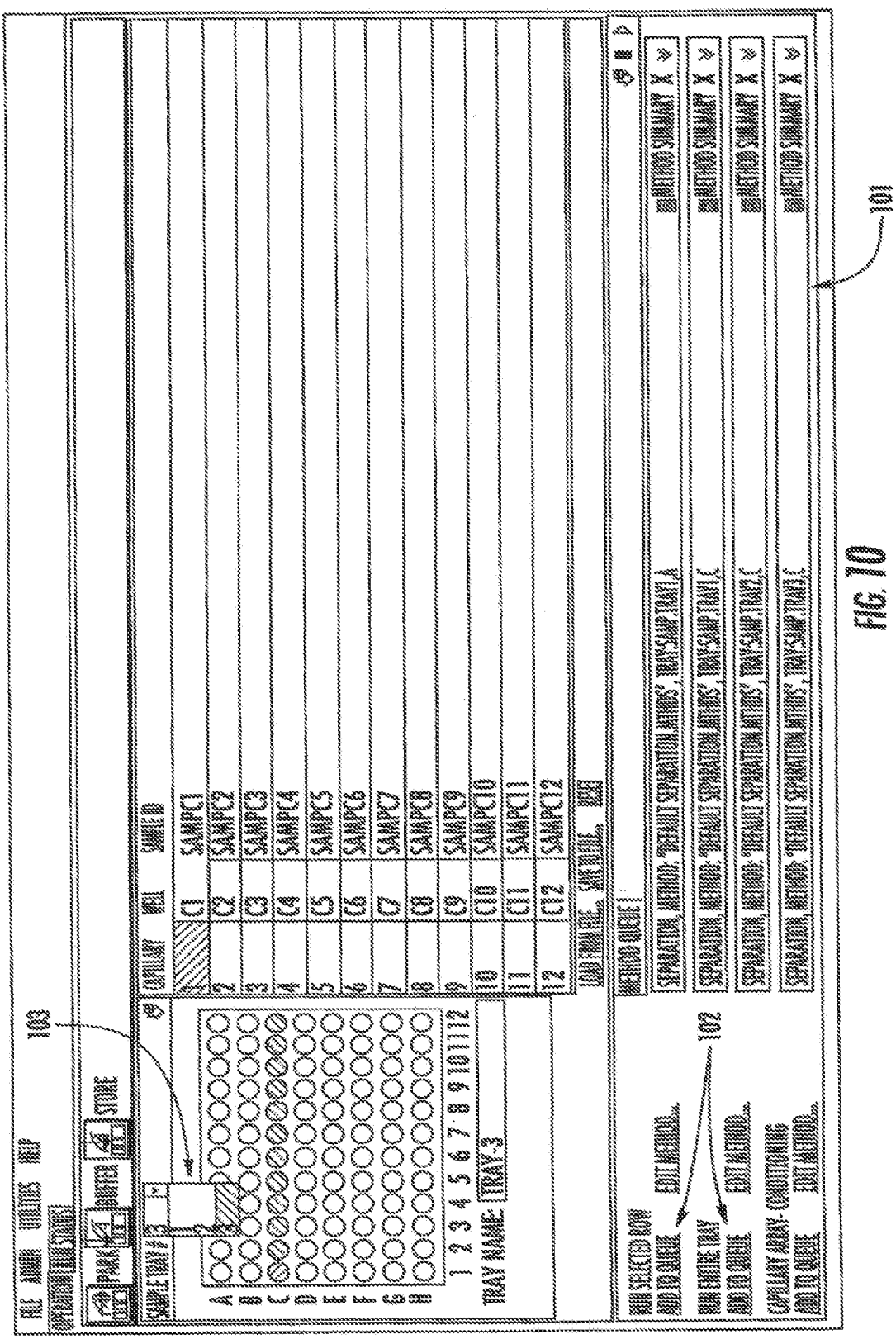
FIG. 10 shows a computer screen image of the computer software.

The graphical result of this computer program is shown in FIG. 10, which shows a list of samples to be analyzed in queue 101, an option to add rows or sample trays 50 to the queue 102, and an option to select the tray number for analysis 103. It is these three aspects that are critical to software portion of the invention: a) Selection of tray 103 (corresponding to a drawer 11 FIG. 1) b) Adding the sample set to a queue (102, FIG. 10) and c) A queue of active samples for analysis (101, FIG. 10), which are executed in sequence until all jobs are complete. Another critical aspect is the ability to add samples to instrument drawers (11, 12 FIG. 1) and queue (101, FIG. 10) while the instrument (system 16) is running other samples.

Figure 14:
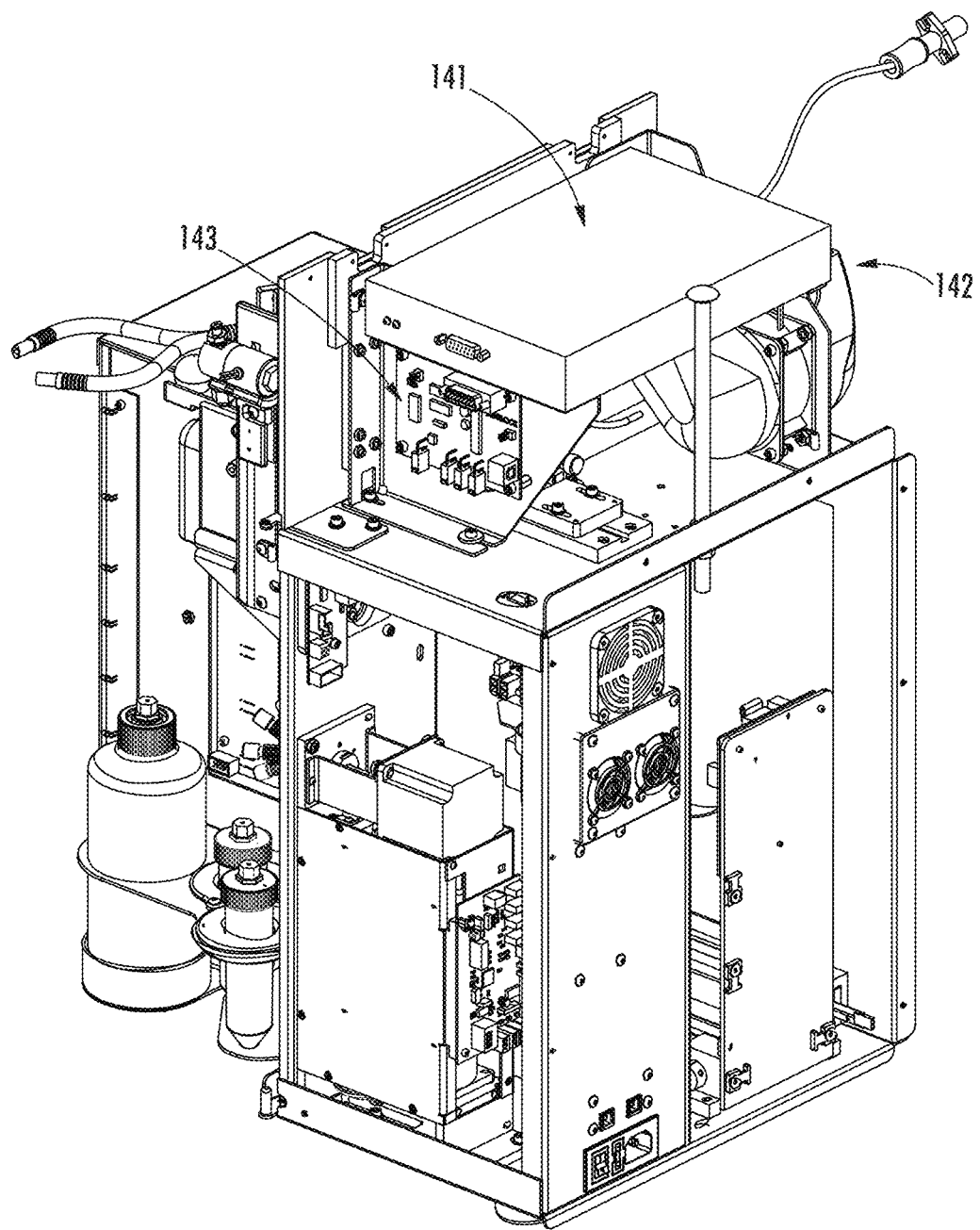
FIG. 14 shows a back view of the instrument with a pulse-field power supply.

FIG. 14 shows a back view of the instrument with a pulse-field high voltage (HV) power supply 141, control electronics 143, and a cooling fan 142 to remove heat generated by the power supply 141. Pulsed field voltage power supply 141 with cooling fan 142 replaces constant-field power supply 65 shown in FIG. 6. A preferred pulse-field power supply is a Ultravolt™ 20HVA24-BP2, 15HVA24-BP2, or 10HVA24-BP2. The output of the power supply 141 is controlled by a control board 143 with variable control voltage. A non-limiting example is a variable control voltage range between plus 10V and minus 10V. The plus 10 V and minus 10 V is scaled to the output of the power supply 141. For a 10 kV power supply 141, the application of a plus 10 V control voltage delivers plus 10 kV from the power supply 141, whereas the application of a minus 10V control voltage delivers minus 10 kV from the power supply 141. An application of plus 5 V to this same 10 kV power supply 141 results in an output voltage of plus 5 kV. For a 20 kV power supply 141, the application of a plus 10V control voltage delivers a plus 20 kV from the power supply 141, whereas an application of plus 5 V results in plus 10 kV voltage from the power supply 141. The control voltage and the associated scaling factor linked with the output of the pulsed-field power supply 141 may be different than the example described above, and is not a critical component of the invention. A waveform generator, which is also a part of control board 143, produces the complex waveforms that result in the variable voltage output of the pulsed-field power supply 141. For example, a plus 7V/minus 4V 10 Hz square wave on the control voltage results in a plus 7 kV/minus 4 kV 10 Hz (Pulse Power) output of the HV pulse power supply 141. The output at one end of the pulsed HV power supply 141 is attached to a multiplex capillary array circuit board 74 through the HV power supply cable 75 as shown in FIG. 8. The output of the return path of the pulsed HV power supply 141 is attached to the outlet electrode (electrode on the reservoir side of the capillaries), which is also connected to ground (or ground electrode) 135 (FIG. 12B).

An embodiment of the present invention is the application of a pulse-field power supply 141 to a multiplex capillary electrophoresis system 16 containing at least two and preferably 12 capillaries 72, so that all capillaries 72 of the multiplex capillary array 17 receive approximately the same pulsed electric field. Another embodiment includes the application of a pulse-field power supply 141 to a capillary electrophoresis system 16 containing at least 24 capillaries 72. An on-board processor (e.g., control electronics or board 143) is used to generate waveforms for the control voltage of any desired shape (square, sine, triangle, sawtooth, etc.). The frequency of the waveform can vary anywhere from <1 Hz to 100 Hz. A preferred frequency range is from 1 Hz to 50 Hz. Another preferred range is from 1 Hz to 20 Hz. An especially preferred range is from 2 Hz to 10 Hz. The control board 143 also has voltage and current monitoring circuitry, so that the voltage applied to the capillary electrophoresis system 16 is actively monitored.

Figure 15A:
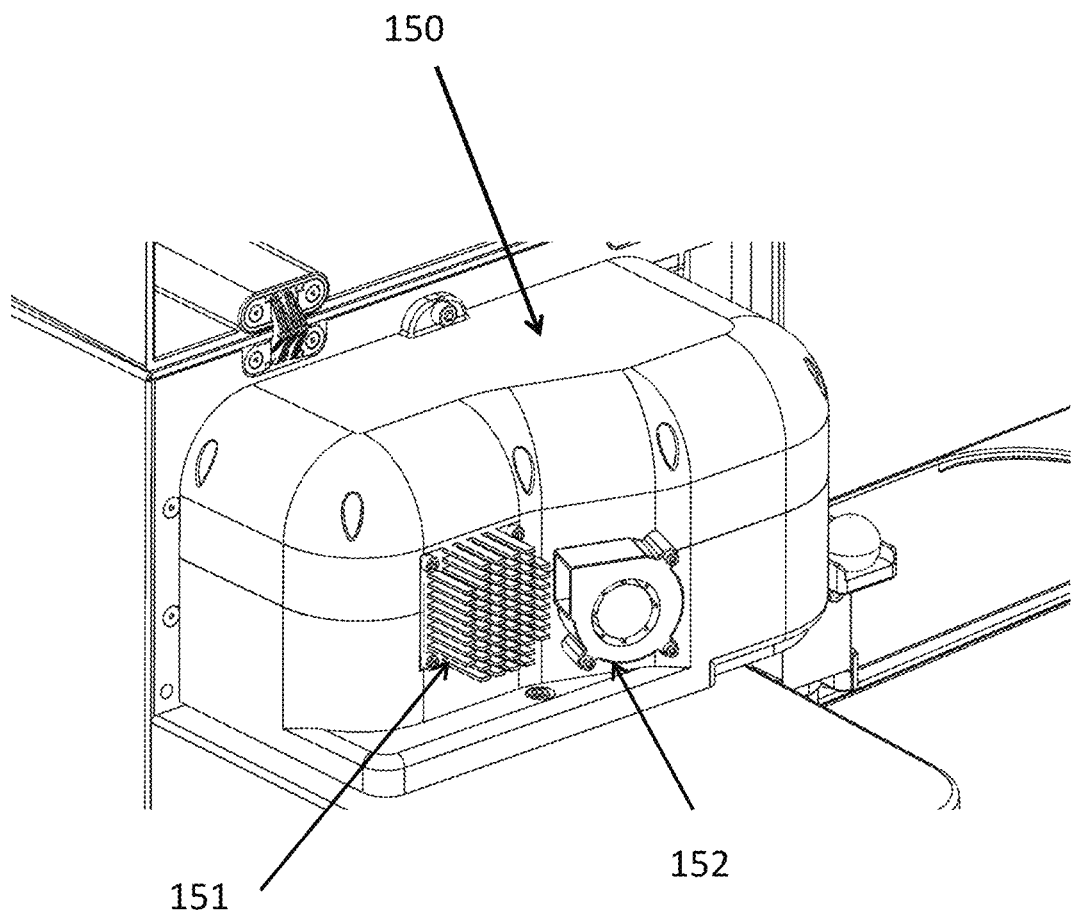
FIG. 15A shows a top view of the instrument with a temperature control chamber.

FIG. 15A shows a top view of the instrument (system 16) with a temperature control chamber 150 with a Peltier cooler 151 and a fan 152 for removing the external heat generated by the Peltier cooler 151. An example Peltier Cooler 151 of the present invention is CP14,127-045 (part number 66101-500) made by Lair Technologies.

Figure 15B:
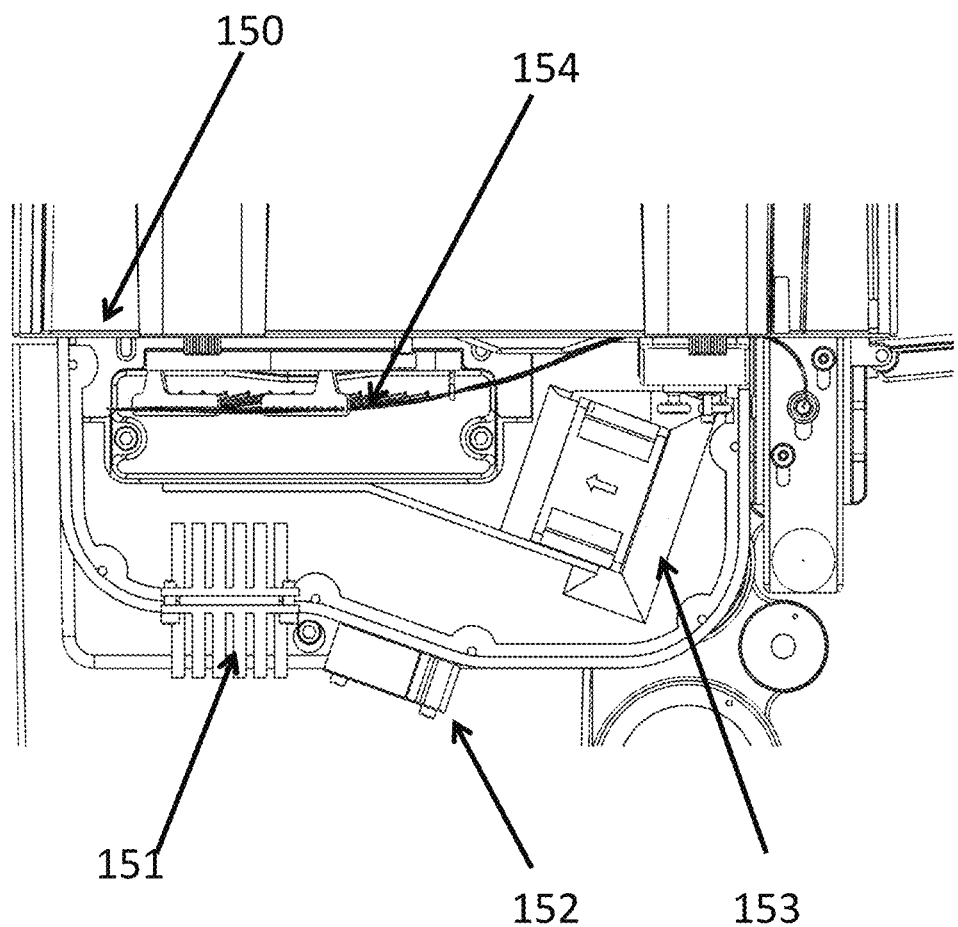
FIG. 15B shows a cutout view of the temperature control chamber.

FIG. 15B shows a top view of the instrument (system 16) with the temperature control chamber 150 with a cutout view, showing the capillary array 154, and internal heating element and air fan 153, which when combined with Peltier cooler 151 enables precise control of the temperature from 10 C. to 25 C.

Iterated Waveforms

For the purposes of this specification, the term "applied waveforms" is equivalent to "applied electric fields". Applying varying pulse-field waveforms across at least two capillaries is identical to applying a pulse-electric field across at least two capillaries.

To better describe varying field waveforms, the following terms are used in this specification:
Common waveforms are square, triangle, sine, and sawtooth, or any combination or blend of waveforms Anode: a positively charged electrode relative to the cathode. The anode may be at a ground voltage, but positive relative to the cathode.

Cathode: a negatively charged electrode, relative to the anode. The cathode may optionally be at a ground voltage, but negative relative to the anode.

Higher pulse voltage: the highest applied voltage of an alternating or varying voltage, over a single cycle of the applied voltage.

Lower pulse voltage: the lowest applied voltage of an alternating or varying voltage, over a single cycle of the applied voltage.

Simple single waveforms are a single waveform shape applied with fixed frequencies and voltages, or optionally varying frequencies and voltages. For example, a simple waveform may consist of a pure sine-wave, with a frequency varying from 50 Hz to 10 Hz over a 60-minute period. A simple waveform may also have asymmetric applied voltage. An example is a square wave with an applied voltage of plus 3 kV to minus 7 kV. A simple waveform may also have varying voltages over time. For example, a sine wave may have higher pulse voltage that may ramp linearly from plus 10 kV to minus 3 kV over a period of time, T, while the lower pulse voltage may ramp linearly from minus 5 kV to minus 1 KV over the same period of time. Thus, the amplitude of the applied Sine wave varies with time. Simple waveforms may also have a forward direction pulse that is identical in time to the reverse-direction pulse. For example, a square wave with plus 5 kV forward pulse of 1 second and minus 6 kV reverse pulse of 1 second. Simple waveforms may also have a forward direction pulse that is different in time to the reverse-direction pulse. For example, a square wave with a plus 5 kV forward pulse of 2 second and minus 6 kV reverse pulse of 1 second.

A simple single waveform may also be a combination of two waveforms superimposed on top of each other to result in unique shape waveforms.

Simple waveforms may have a duration of the higher pulse voltage longer or shorter than the duration of the lower pulse voltage. The ratio of the length of one side of the pulse, relative to the total time of a pulse cycle, expressed as a percent, is often referred to or expressed as the "duty cycle" of the pulse. For example, a 50% duty cycle would define a higher pulse voltage time (T1) equal to a lower pulse voltage time (T2). The relative duty of the positive pulse is (T1*100/(T1+T2)). For T1=T2, the duty cycle is 50%. For T1 ⅓ the time of T2, the duty cycle is (1*100/(1+3))=25%. Directional flow is achieved in electrophoresis by applying a higher pulse voltage longer the lower pulse voltage (or vice versa). For example, a plus/minus 5 kV 1 Hz square wave applied to an electrophoresis column may have 0.66 seconds at plus 5 kV and 0.33 seconds at minus 5 kV for a 66% duty cycle.

One aspect of the present invention is the application of complex waveforms, which is defined as the application of sequences of simple waveforms that are iterated for the duration of the analytical run.

Figure 18A:
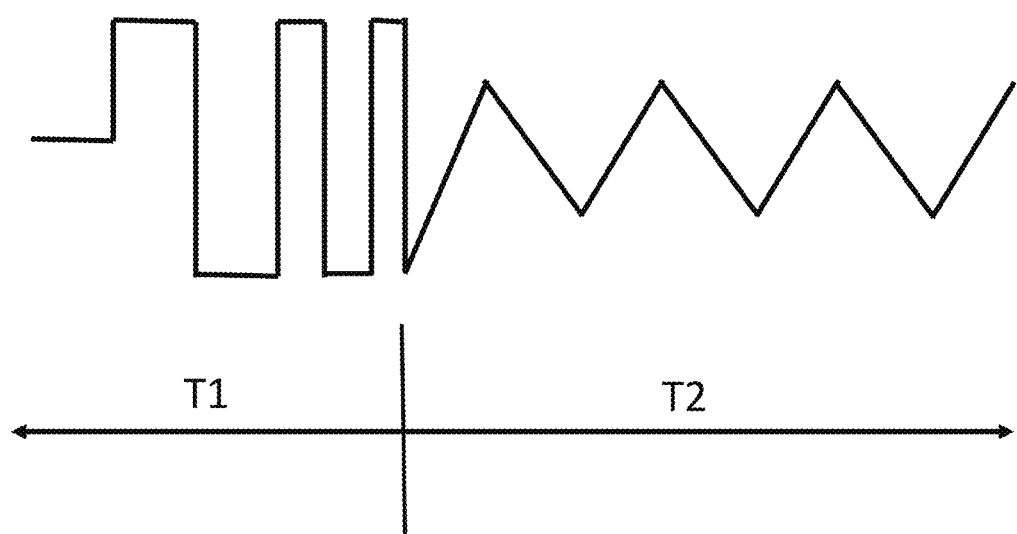
FIG. 18A shows an example of a square wave applied for a period of time T1, followed by a triangle wave applied for a time T2
Figure 18:
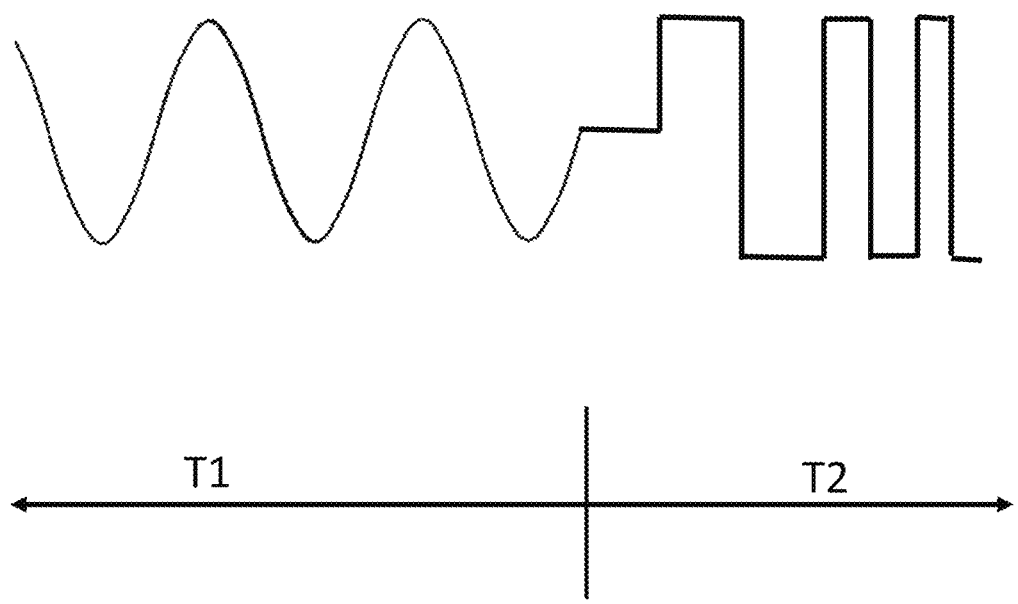
FIG. 18B shows an example of a sine wave applied for a period of time T1, followed by a square wave applied for a time of T2.

A preferred method for obtaining high-quality separations of complex DNA smears using multiplex pulsed-field parallel capillary electrophoresis is to apply different variable voltage waveform patterns, or simple waveforms, in sequence, over time, in repeated iterations. For example, a preferred separation method is to apply a square wave for a period of time followed by a triangle wave for a period of time, and then repeating the square-wave and triangle-wave sequence for several iterations. This is shown in FIG. 18A, with a square wave applied for a period of time, T1, followed by a triangle wave, applied for a period of time, T2. In the case shown in FIG. 18A, the frequency of the applied square wave varies from slow to fast, while the frequency of the triangle wave is constant. FIG. 18B shows a sine wave (fixed frequency) applied for a period of time, T1, followed by a square wave of varying frequency for a period of time T2. The T1+T2 sequence is iterated for "I" times to obtain a total run time of I(T1+T2) minutes. Another example is to apply a square wave for a period of time followed by a constant voltage for a period of time, and then iterating the square-wave and constant voltage sequence for several iterations. Another preferred aspect of the invention is to apply at least three different waveforms over the period of the electrophoresis separation. For example, the application of a triangle wave, followed by a square wave, followed by a sine wave, with the sequence of the three waveforms iterated multiple times. Another preferred aspect of the invention is to iterate two different waveforms, followed by a third waveform. For example, the application of a triangle wave, followed by a square wave, the sequence of which is iterated several times, followed by the application of a square wave for a fixed period of time. Another example is to apply a square wave, for a first period of time, a constant voltage for a second period of time, and triangle wave for a third period of time, in sequential segments, and iterate the sequence multiple times until the electrophoresis run is complete.

Another preferred method for obtaining high-quality separations is to apply different waveform patterns over time, and apply a varying frequency or varying voltage ramp, or a combination of both, to the electrophoretic separation.

Another preferred method uses shorter periods of time for the frequency ramp. For example, a square wave varying from plus 250 V/cm to minus 100 V/cm with a frequency ramp of 15 Hz down to 0.5 Hz over a period of 30 seconds, followed by a Triangle wave varying from plus 250 V/cm to minus 100 V/cm with a frequency ramp of 10 Hz to 5 Hz over a period of 30 seconds, with the square/triangle wave sequence iterated 90 times for a total run time of 90 minutes.

The time range for each applied wave form varies from 0.5 seconds up to 20 minutes. A preferred range is from 15 seconds to 10 minutes. An even more preferred time frame is from 10 seconds to 120 seconds.

The frequency range for each applied wave form varies from 100 Hz to 0.5 Hz. A preferred frequency range is from 30 Hz to 0.5 Hz. Another preferred range is from 20 Hz to 2 Hz. It is preferable to ramp the frequency over the time period of each applied waveform. For example, if a square wave is applied for 1 minute, the frequency is ramped from 2 Hz to 15 Hz or from 15 Hz to 2 Hz over the same 1 minute timeframe. The output of the pulsed-field HV power supply is connected to the inlet electrodes through circuit board 74 (the set of electrodes on the sample or buffer tray side of the capillary array) as shown in FIG. 8, whereas the outlet electrode (electrode on the reservoir side of the capillaries) is connected to ground 135 FIG. 12B, which is also the return path of the pulsed-field HV power supply.

A preferred process for performing multiplex capillary electrophoresis of the present invention is to fill at least two capillaries 72 with conductive medium containing a sieving matrix, introduce a sample into the capillaries 72 through either electrokinetic injection or hydrodynamic injection (i.e. by vacuum injecting or pressure injecting a sample into the capillaries 72), apply a varying voltage of the present invention via a pulse-field power supply across the capillaries 72 to induce separation of the sample, and then detect the sample as it passes through the windows 79 of the capillaries 72 by fluorescence or absorption detection.

One preferred method of applying a varying electric field across at least two capillaries comprises; applying a first pulse-field waveform at a first frequency across said capillaries for a first period of time; applying at least a second, different shape pulse-field waveform at a second frequency across said capillaries for a second period of time; thereafter repeating the said first and at least second pulse-field waveform at least twice; wherein said first frequency varies with time within said first period of time and said second frequency varies with time within said second period of time.

Example 1

Figure 16A:
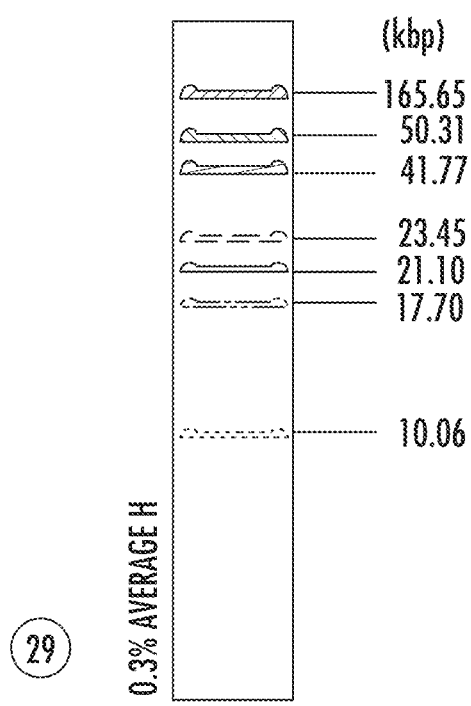
FIG. 16A shows a prior-art slab-gel separation of Marker 7GT
Figure 16B:
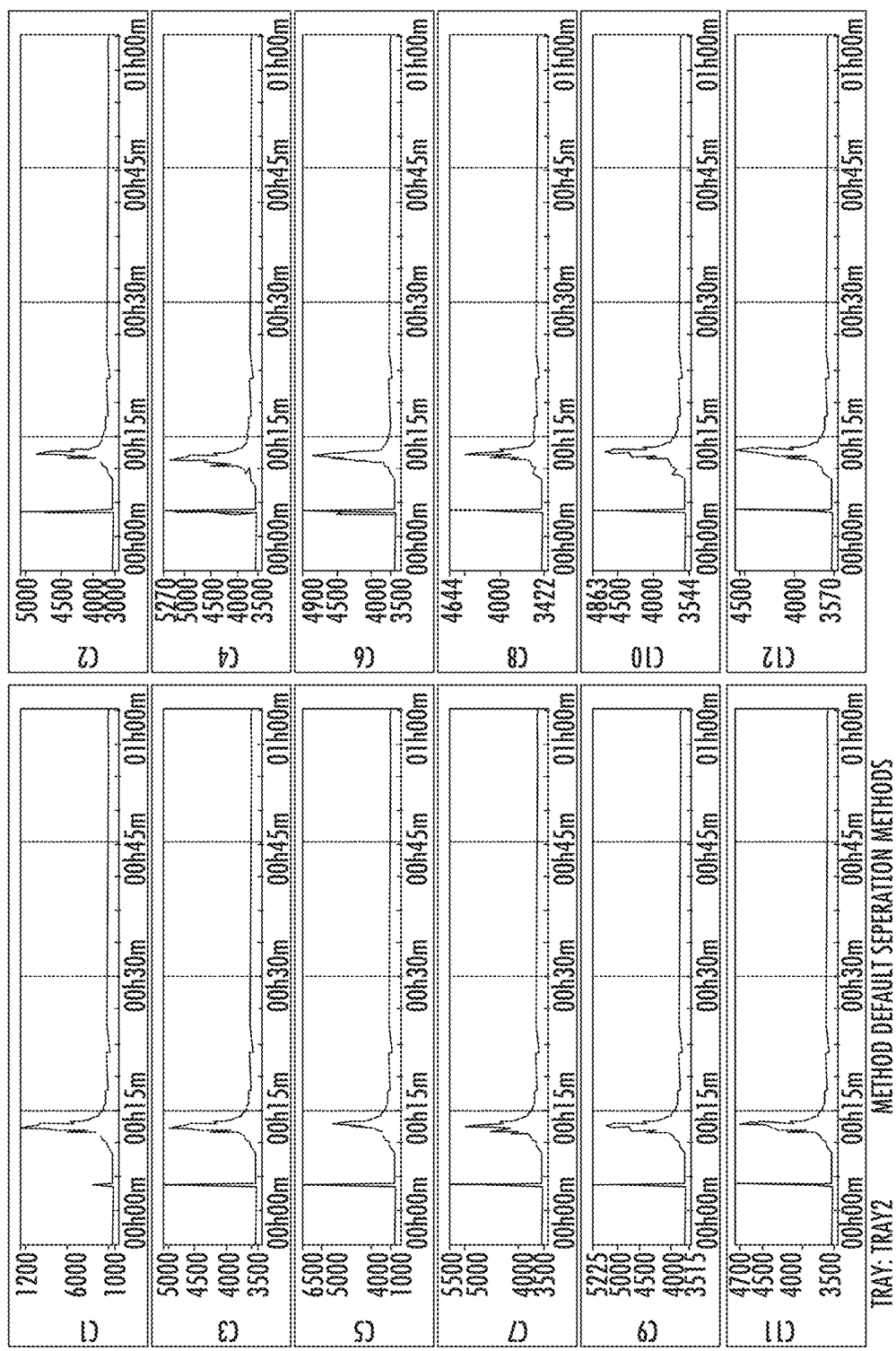
FIG. 16B shows the separation of Marker 7GT using prior-art capillary electrophoresis with constant applied electric field.
Figure 16C:
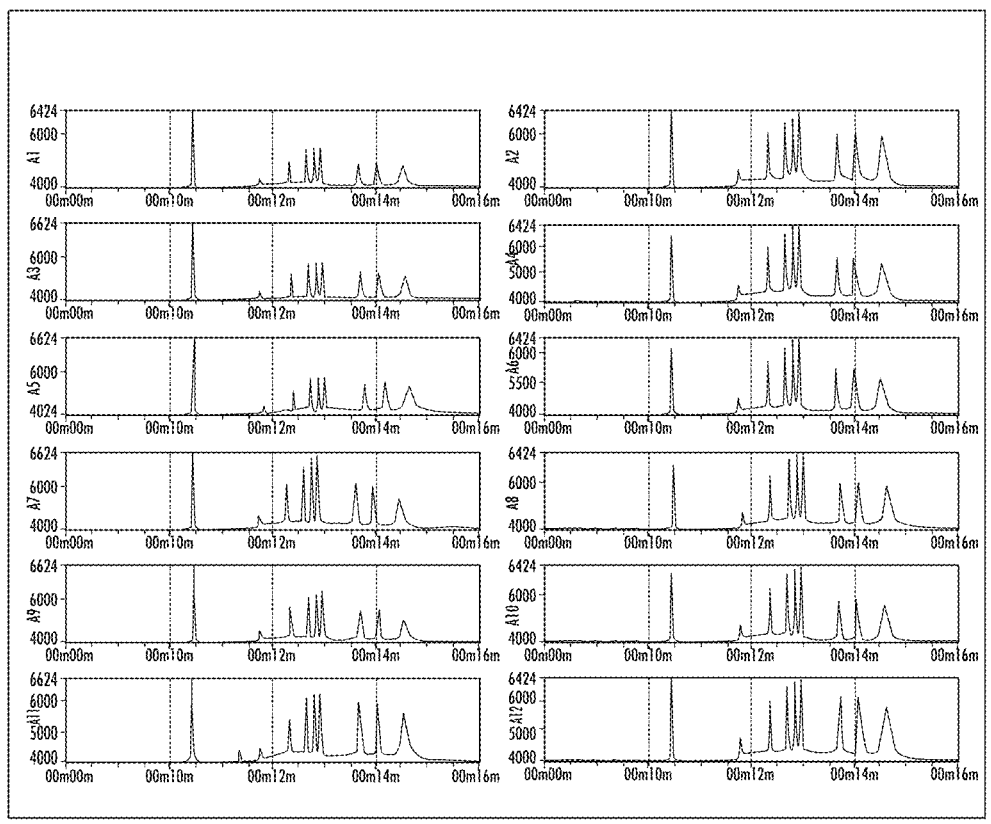
FIG. 16C shows the separation of Marker 7GT using the capillary electrophoresis system of the present invention with a pulsed applied electric field.

A pulse-field capillary electrophoresis gel "930 Gel" (available from Advanced Analytical Technology) was used for this example. The "930 Gel" sieving matrix was pumped into a plurality twelve capillaries with an effective length of 22 cm and a total length of 40 cm (50 um I.D.) using the capillary electrophoresis system described in this specification. A 7GT DNA sizing ladder (Available from Wako Chemical Company) comprised of DNA fragments with sizes of 10.06 kB, 17.7 kB, 21.2 kB, 23.45 kB, 41.77 kB, 50.31 kB, and 165.65 kB (FIG. 16A) was used to evaluate separation efficiency on a capillary electrophoresis system. A sample of 150 pg/µL of the 7GT ladder in 1×TE Buffer was prepared as a sample for analysis. The gel-filled capillaries were treated with an electrophoresis pre-run by applying 2.0 kV for 1 second prior to injection of sample. The 7GT ladder sample was injected onto the capillary electrophoresis system (present invention) using an electrokinetic injection of 5 kV for 5 sec. This was immediately followed by an electrophoresis run using a constant applied voltage of 7.2 kV for 3600 seconds, with the resulting electropherogram shown in FIG. 16B. This represents a best-case separation for prior-art constant-field capillary electrophoresis systems. The same sample (same injection, same concentration), was then re-analyzed using the capillary electrophoresis system of the present invention, but with pulsed-field applied voltage of plus 1.8 kV/minus 7.2 kV with a 5 Hz Square Wave. The resulting set of electropherograms for the 12-capillary system is shown in FIG. 16C. The ambient temperature for all analysis (both constant field and pulsed-field) was approximately 23 C. Separation with a Pulsed-field (FIG. 16C) shows a much better baseline resolved electropherogram, with all 7 of the ladder elements clearly visible relative to the separation using prior-art constant-field (FIG. 15), which shows a single, merged peak.

For this example, 12 capillaries were run simultaneously with the same applied constant or pulsed field.

Example 2

Figure 17A:
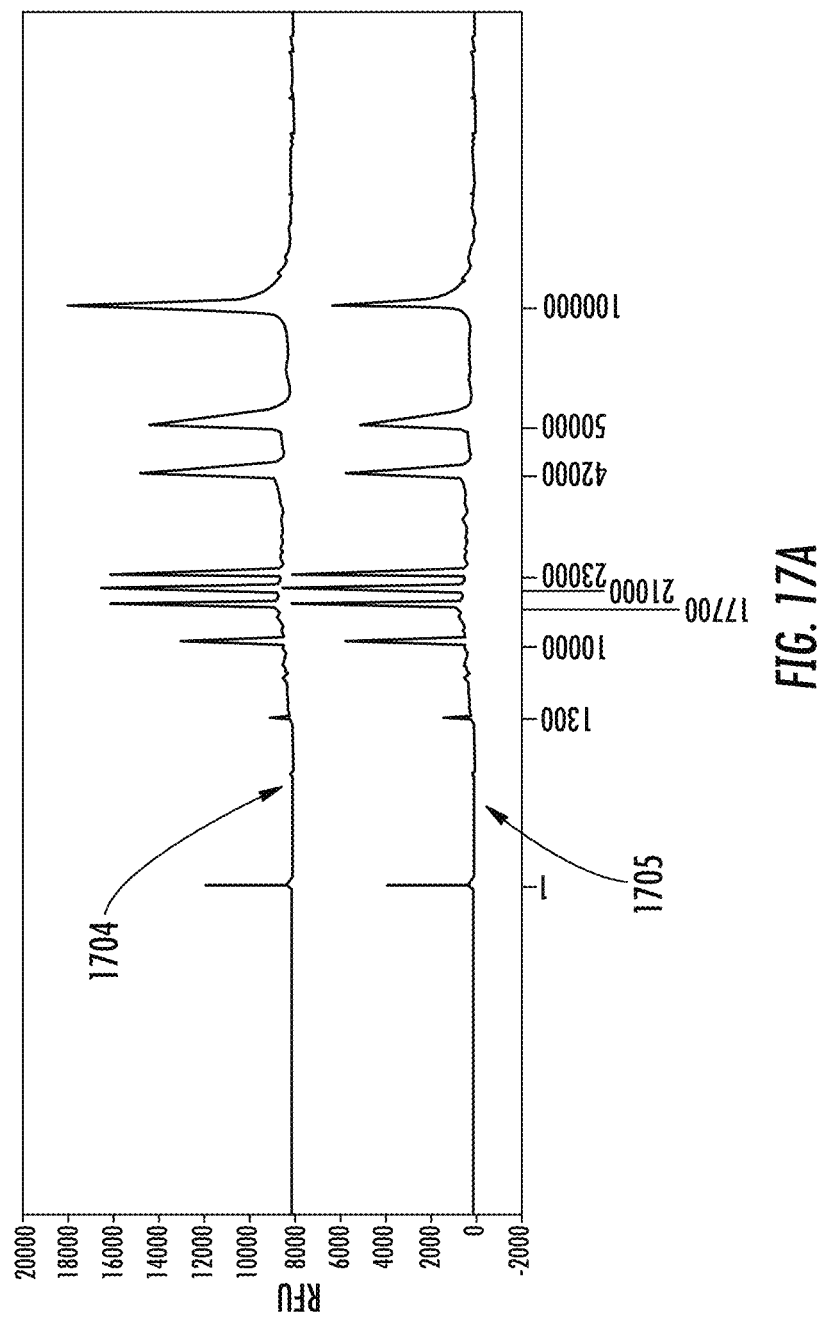
FIG. 17A shows the separation of Marker 7GT using both a pure square wave (bottom trace) and a mixed square/triangle wave (top trace).

A pulse-field capillary electrophoresis gel "FP 5001 Large DNA Separation Gel" (available from Advanced Analytical Technology) was used for this example. The "FP 5001 Large DNA Separation Gel" sieving matrix was pumped into a plurality twelve capillaries with an effective length of 22 cm and a total length of 40 cm (50 um I.D.) using the capillary electrophoresis system described in this specification. A 7GT DNA sizing ladder (Available from Wako Chemical Company) comprised of DNA fragments with sizes of 10.06 kB, 17.7 kB, 21.2 kB, 23.45 kB, 41.77 kB, 50.31 kB, and 165.65 kB (FIG. 16A) was used to evaluate separation efficiency on a capillary electrophoresis system. A sample of 150 pg/µL of the 7GT ladder in 1×TE Buffer was prepared as a sample for analysis by dilution in 0.25× Tris-EDTA buffer. The gel-filled capillaries were treated with an electrophoresis pre-run by applying 2.0 kV for 1 second prior to injection of sample. The 7GT ladder sample was injected onto the capillary electrophoresis system (present invention) using an electrokinetic injection of minus 5 kV for 5 sec. This was immediately followed by an electrophoresis run using two different conditions. FIG. 17A (Top trace-1704) was obtained using an applied voltage consisting of a Triangle Wave (plus 2.0 kV to minus 7.2 kV) with a frequency of 2 to 7 Hz, varied linearly over a period of 30 seconds, followed by a square wave (plus 2.0 kV to minus 7.2 kV) with a frequency of 2 to 7 Hz, varied linearly over a period of 30 seconds. The Triangle wave (30 seconds) followed by Square wave (30 seconds) was iterated for 100 times for a total run time of 100 min. FIG. 17A (bottom trace 1705) was obtained using an applied voltage consisting of a Square Wave (plus 2.0 kV to minus 7.2 kV) with a frequency of 2 to 7 Hz, varied linearly over a period of 30 seconds. The Square wave (30 seconds) was iterated for 200 times for a total run time of 100 min. For the 7GT ladder traces, the fragment separation was similar for both the top trace and the bottom trace, indicating that the application of the iterated triangle/square waveform (FIG. 17A top trace) did not substantially affect the separation of the 7GT fragments, as compared to a pure square-wave method without iterations (FIG. 17A lower trace).

Figure 17B:
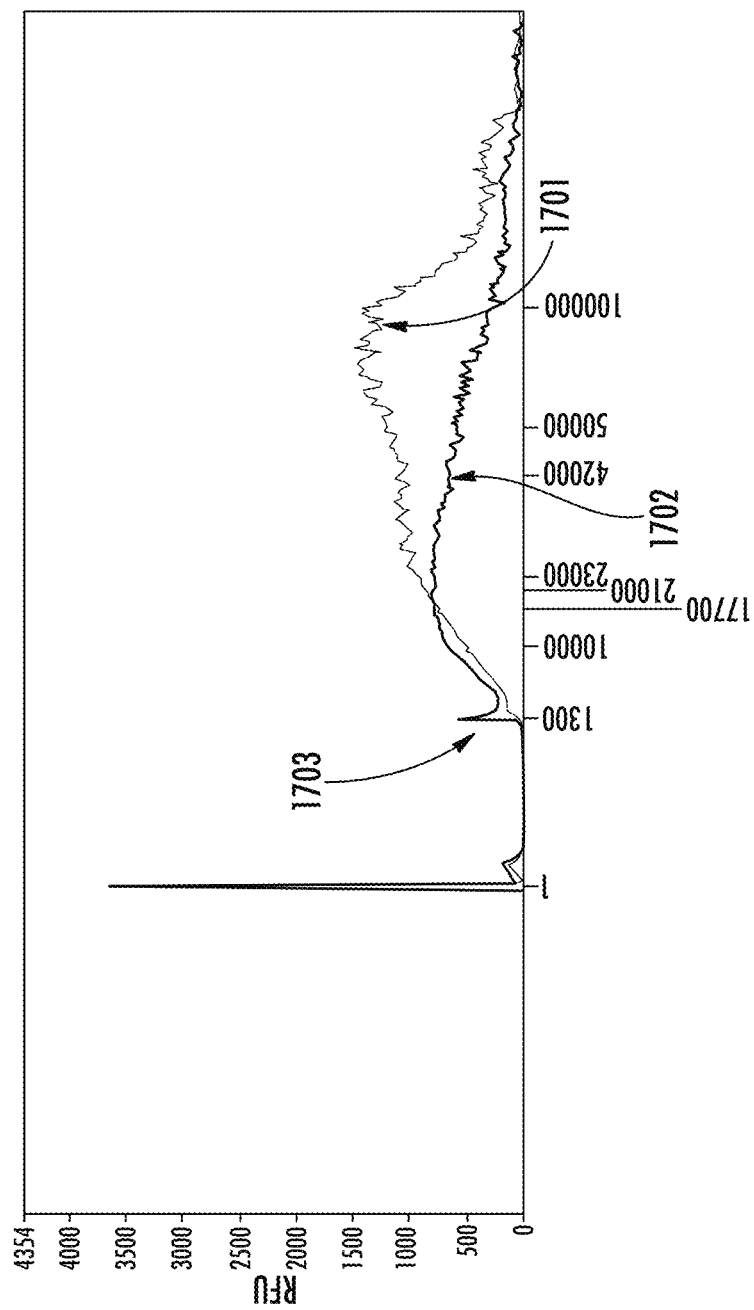
FIG. 17B shows an electropherogram of a DNA smear analyzed with an iterated mixed wave sequence, compared with the electropherogram of the same DNA smear analyzed with a pure square wave.

These same set of waveforms were applied to the separation of a DNA smear. A gDNA sample (Sample A) was diluted to 150 pg/µL in 0.25 Tris-EDTA buffer. The gel-filled capillaries were treated with an electrophoresis pre-run by applying 2.0 kV for 1 second prior to injection of sample. Sample A was injected onto the capillary electrophoresis system (present invention) using an electrokinetic injection of minus 5 kV for 5 sec. This was immediately followed by an electrophoresis run using two different conditions. FIG. 17B (Trace 1701) was obtained using an applied voltage consisting of a Triangle Wave (plus 2.0 kV to minus 7.2 kV) with a frequency of 2 to 7 Hz, varied linearly over a period of 30 seconds, followed by a square wave (plus 2.0 kV to minus 7.2 kV) with a frequency of 2 to 7 Hz, varied linearly over a period of 30 seconds. The Triangle wave (30 seconds) followed by Square wave (30 seconds) was iterated for 100 times for a total run time of 100 min. FIG. 17B (Trace 1702) was obtained using an applied voltage consisting of a Square Wave (plus 2.0 kV to minus 7.2 kV) with a frequency of 2 to 7 Hz, varied linearly over a period of 30 seconds. The Square wave (30 seconds) was iterated for 200 times for a total run time of 100 min. Note that the trace 1701 had a much higher average smear size of 73,692 bp vs. trace 1702 with an average smear size of 53,478 bp. Also, the trace 1701 (FIG. 17B) obtained with the triangle/square iterated blend shows no anomalous system peak 1703 (FIG. 17B). The actual size of Sample A is roughly 70 kpb as determined by normal Pulse-Field slab gel electrophoresis, which matches the results obtained with the pulse-field capillary system of the present invention.

As can be seen from the above description, the pulsed-field multiplex capillary electrophoresis system of the present invention allows for the multiplexed, enhanced separation of fragments with sizes up to >150 kB, compared to prior-art constant-field multiplex capillary electrophoresis systems.

What is claimed is:

1. A method for multiplex capillary electrophoresis, the method comprising:
    applying a sequence of waveforms by:
        applying a first pulse-field waveform at a first frequency across each of two capillaries for a first period of time, each of the two capillaries containing molecular species in a medium; and
        applying at least a second, different shape pulse-field waveform at a second frequency across each of the two capillaries for a second period of time immediately following the first period of time;
    repeating the applying of the sequence of waveforms at least twice; and
    detecting and identifying the molecular species in each of the two capillaries from molecular species migration within each of the two capillaries.

2. The method of claim 1, wherein said first frequency varies with time within said first period of time and said second frequency varies with time within said second period of time.

3. The method of claim 1, wherein the first pulse-field waveform and the second pulse-field waveform are selected from the group consisting of: a square wave; a triangle wave; a sine wave; and a sawtooth wave.

4. The method of claim 1, wherein the first period of time and the second period of time are selected from the group consisting of: less than 10 minutes each; less than 5 minutes each; and less than 1 minute each.

5. The method of claim 1, comprising detecting a sample in windows of said capillaries by fluorescence or absorption detection.

6. The method of claim 1, wherein the first frequency and the second frequency vary in a range selected from the group consisting of: 0.5 Hz to 100 Hz; 0.5 Hz to 15 Hz; 0.5 Hz to 30 Hz; 2 Hz to 20 Hz; and 2 Hz to 15 Hz.

7. The method of claim 1, wherein the first pulse-field waveform and the second pulse-field waveform are effective to electrophoretically separate nucleic acids of the sample having fragment sizes greater than 150,000 base pairs (bp) in the capillary array.

8. The method of claim 1, comprising a feature selected from the group consisting of:
    the first pulse-field waveform and the second pulse-field waveform are applied across each of twelve capillaries containing molecular species, wherein the molecular species in each of the twelve capillaries are detected and identified; and
    the first pulse-field waveform and the second pulse-field waveform are applied across each of twenty-four capillaries containing molecular species, wherein the molecular species in each of the twenty-four capillaries are detected and identified.

9. A method of multiplex capillary electrophoresis, comprising:
    applying a sequence of waveforms by:
        applying a first pulse-field waveform at a first frequency across each of two capillaries for a first period of time, each of the two capillaries containing molecular species in a medium;
        applying a second, different shape pulse-field waveform across each of the two capillaries at a second frequency for a second period of time immediately following the first period of time; and
        applying at least a third pulse-field waveform across each of the two capillaries at a third frequency for a third period of time, the third pulse-field waveform having a shape different from at least one of the first pulse-field waveform or the second pulse-field waveform;
    repeating the applying of the sequence of waveforms at least twice; and
    detecting and identifying the molecular species in each of the two capillaries from molecular species migration within each of the two capillaries.

10. The method of claim 9, wherein said first frequency varies with time within said first period of time, said second frequency varies with time within said second period of time, and said third frequency varies with time within said third period of time.

11. A multiplex capillary electrophoresis system for multiplex pulse-field electrophoresis, the multiplex capillary electrophoresis system comprising:
    a console configured to house a replaceable capillary array comprising two capillaries;
    a pulse-field alternating current power supply disposed in the console; and
    a control device configured to control the pulse-field alternating current power supply to:
        apply a sequence of waveforms by:
            applying a first pulse-field waveform at a first frequency across each of at least two capillaries for a first period of time; and
            applying at least a second, different shape pulse-field waveform at a second frequency across each of the two capillaries for a second period of time immediately following the first period of time, and
        repeat the applying of the sequence of waveforms at least twice; and
    a detector disposed in the console, and configured to detect molecular species in each of the two capillaries from molecular species migration within each of the two capillaries.

12. The multiplex capillary electrophoresis system of claim 11, wherein the console comprises an injection position under which the capillary array is received, and the console is configured to receive a sample plate at the injection position, the sample plate configured to contain a sample that comprises the molecular species, wherein:
    the console is configured to, at the injection position, inject a sample into the capillary array; and
    the pulse-field alternating current power supply is configured to, after injection of the sample, apply the first pulse-field waveform and the second pulse-field waveform to effect electrophoretic separation of the sample.

13. The multiplex capillary electrophoresis system of claim 12, wherein, at the injection position, the pulse-field alternating current power supply is configured to, before applying the first pulse-field waveform and the second pulse-field waveform, apply an electric field effective to inject the sample into the capillary array.

14. The multiplex capillary electrophoresis system of claim 12, wherein the console is configured to inject the sample hydrodynamically.

15. The multiplex capillary electrophoresis system of claim 11, comprising:
    at least two drawers disposed in the console, and configured to contain separately at least a buffer plate and a sample plate; and
    a motion control system disposed in the console, and configured to move at least one of the sample plate or the buffer plate from at least one of the at least two drawers to an injection position of the multiplex capillary electrophoresis system.

16. The multiplex capillary electrophoresis system of claim 11, wherein the pulse-field alternating current power supply is configured to apply at least a third pulse-field waveform across each of the two capillaries at a third frequency for a third period of time.

17. The multiplex capillary electrophoresis system of claim 11, comprising a waveform generator communicating with the pulse-field alternating current power supply, and configured to generate the first pulse-field waveform and the second pulse-field waveform.

18. The multiplex capillary electrophoresis system of claim 11, comprising a capillary array circuit board communicating with the pulse-field alternating current power supply, wherein the pulse-field alternating current power supply is configured to apply the first pulse-field waveform and the second pulse-field waveform via the capillary array circuit board.

19. The multiplex capillary electrophoresis system of claim 18, further comprising an electrode array communicating with the capillary array circuit board, wherein the pulse-field alternating current power supply is configured to apply the first pulse-field waveform and the second pulse-field waveform further via the electrode array.

20. The multiplex capillary electrophoresis system of claim 19, wherein the capillaries comprise respective capillary tips, and the electrode array comprises electrodes disposed adjacent to the respective capillary tips.

* * * * *